(12) United States Patent
Takamizawa et al.

(10) Patent No.: US 7,315,030 B2
(45) Date of Patent: Jan. 1, 2008

(54) LASER SCANNING MICROSCOPE, STORAGE MEDIUM STORING SPECTRAL DATA ACQUISITION PROGRAM, AND SPECTRAL DATA ACQUISITION METHOD

(75) Inventors: Nobuhiro Takamizawa, Sagamihara (JP); Yujin Arai, Tokyo (JP)

(73) Assignee: Olympus Corporation, Tokyo (JP)

( * ) Notice: Subject to any disclaimer, the term of this patent is extended or adjusted under 35 U.S.C. 154(b) by 103 days.

(21) Appl. No.: 11/185,374

(22) Filed: Jul. 20, 2005

(65) Prior Publication Data

US 2006/0017006 A1    Jan. 26, 2006

(30) Foreign Application Priority Data

Jul. 26, 2004   (JP)   ............................. 2004-217397

(51) Int. Cl.
G01N 21/64    (2006.01)
G21H 3/02     (2006.01)

(52) U.S. Cl. ................. 250/458.1; 250/459.1
(58) Field of Classification Search ............. 250/458.1, 250/459.1
See application file for complete search history.

(56) References Cited

U.S. PATENT DOCUMENTS 6,300,639 B1    10/2001   Wiederhoeft

2003/0179372 A1*   9/2003   Knebel ..................... 356/318

FOREIGN PATENT DOCUMENTS

JP    2000-39563 A    2/2000

* cited by examiner

Primary Examiner—David Porta
Assistant Examiner—Mindy Vu
(74) Attorney, Agent, or Firm—Frishauf, Holtz, Goodman & Chick, P.C.

(57) ABSTRACT

A laser scanning microscope enables an observation of a specimen through emitting a laser beam onto the specimen marked by a plurality of fluorescent probes and receiving a fluorescent light back from the specimen corresponding to the emission, and comprises a laser source for generating a laser beam in an excitation wavelength corresponding to the plurality of fluorescent probes, a deflector unit for scanning the generated laser beam over an observation plane of the specimen, a dispersion unit for dispersing a fluorescent light from the specimen to extract it by an arbitrary wavelength interval, a spectral data acquisition condition setting unit for setting a condition for the dispersion unit acquiring a spectral data based on spectrum characteristics of the plurality of fluorescent probes, a dispersion control unit for controlling the dispersion unit based on the set spectral data acquisition condition.

24 Claims, 22 Drawing Sheets

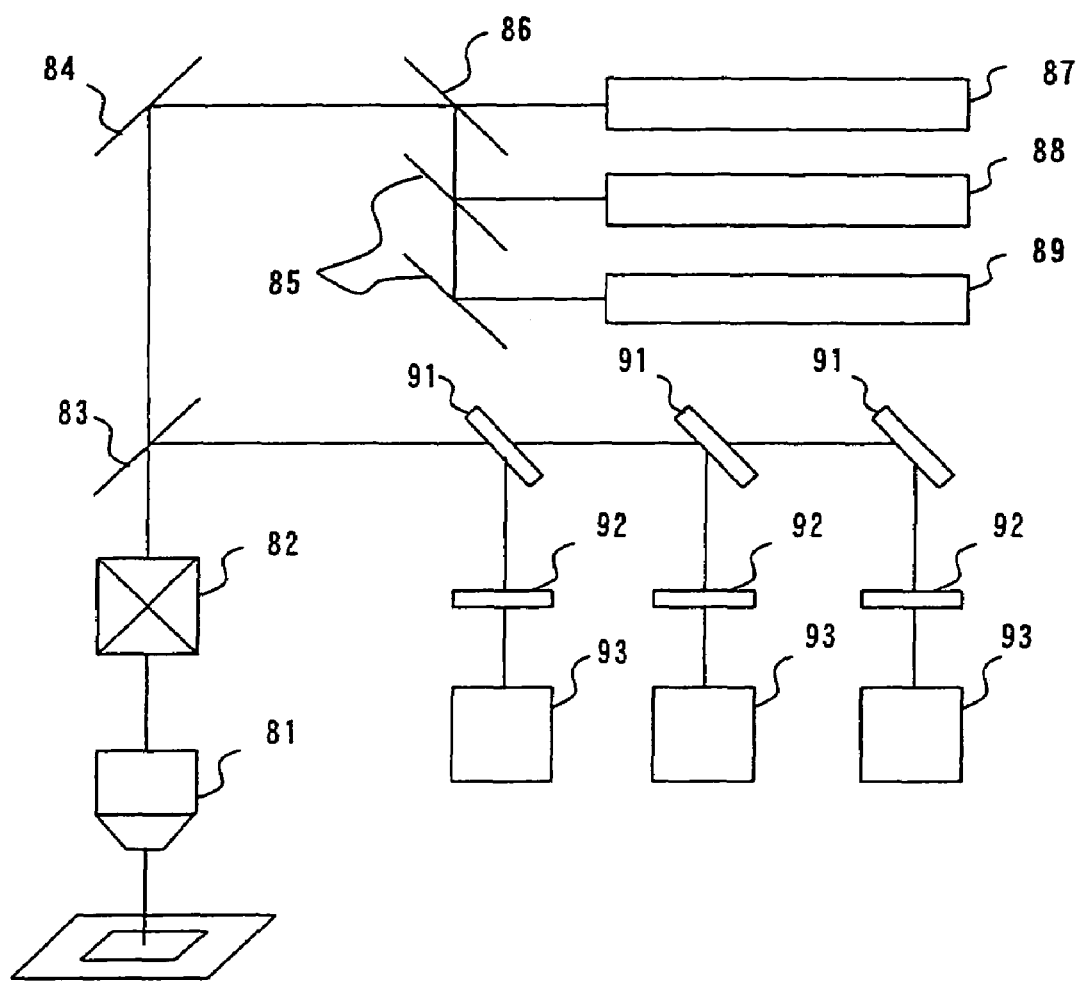
F I G. 1

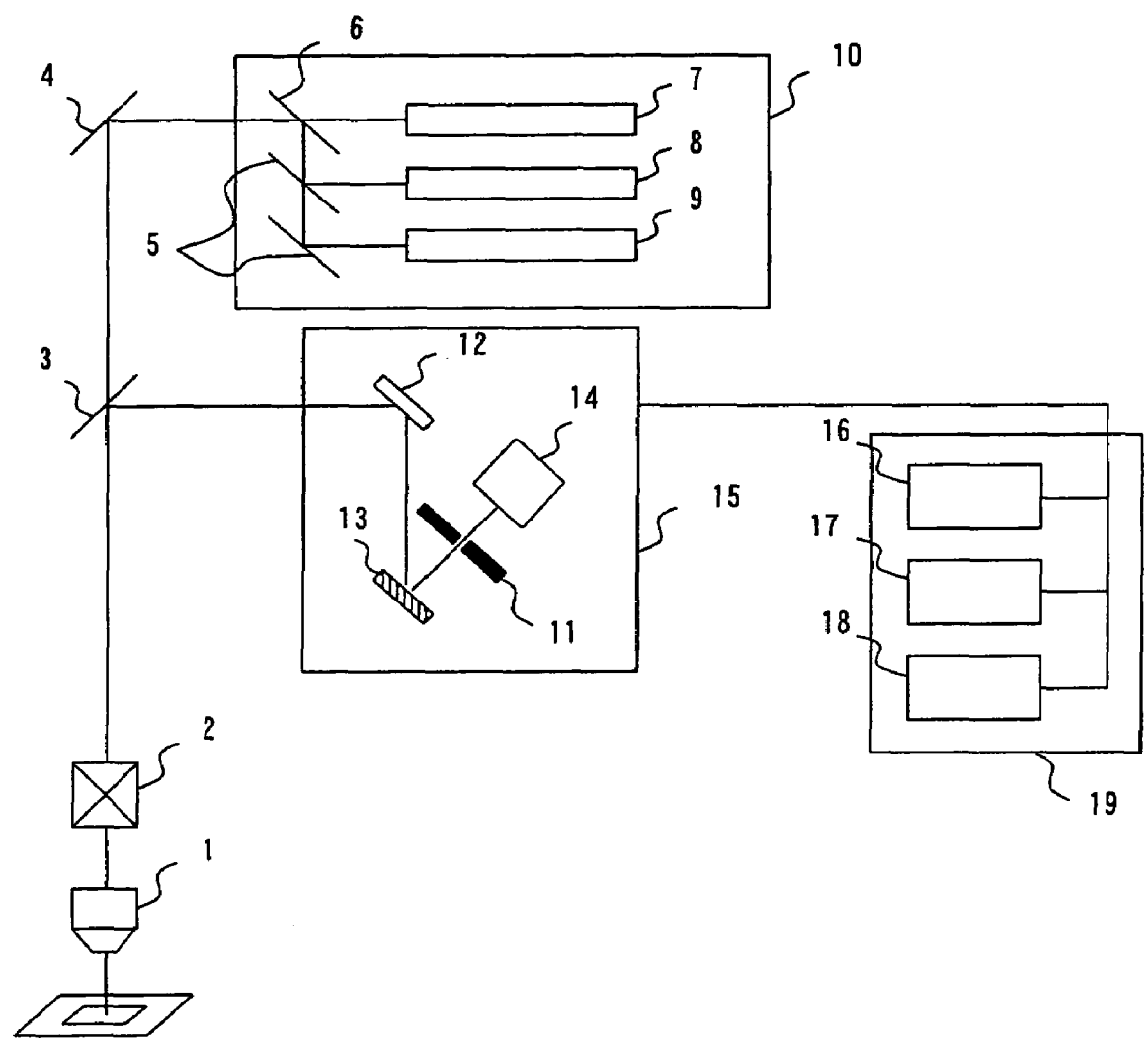
F I G. 2

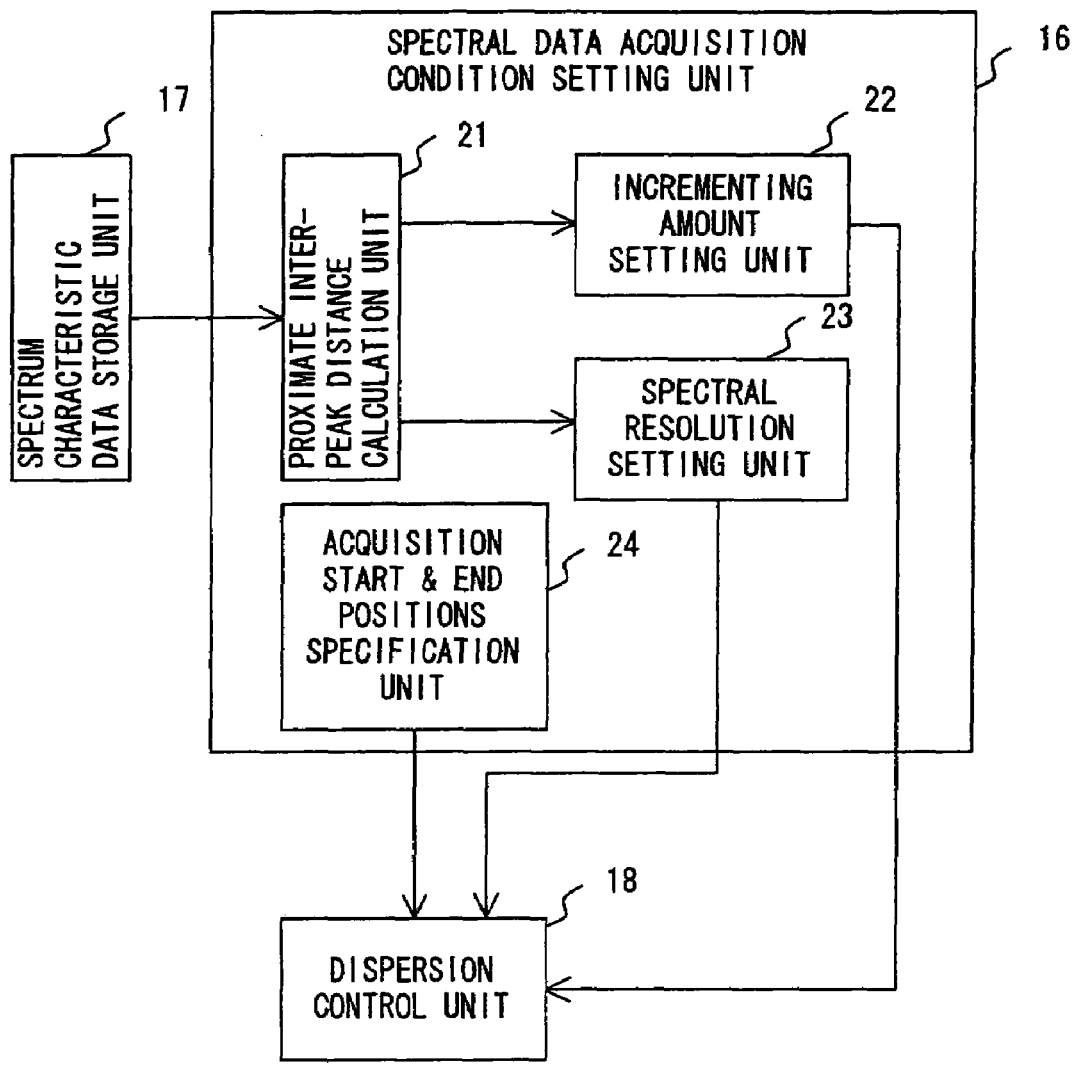
F I G. 3

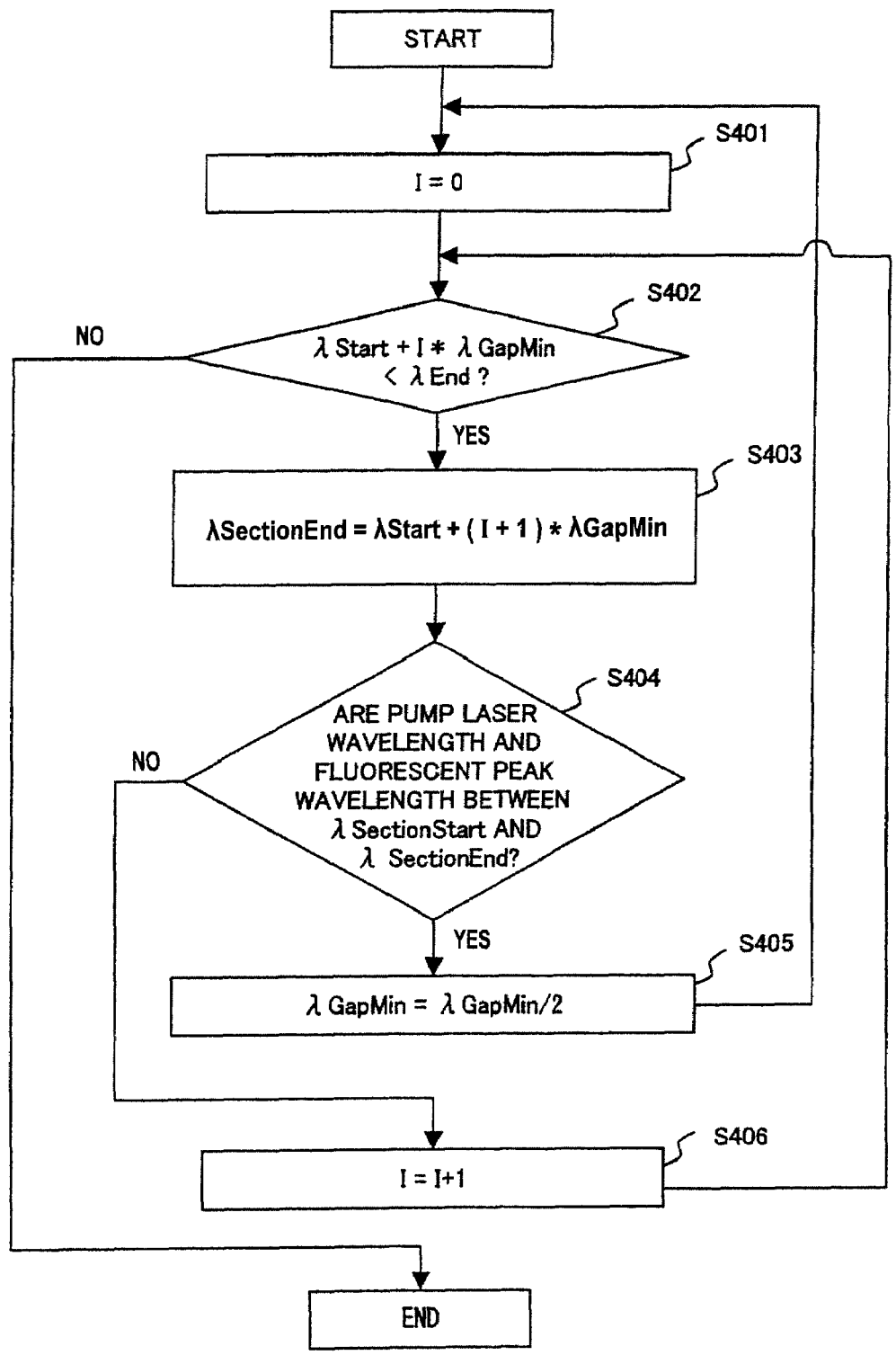
F I G. 1 2

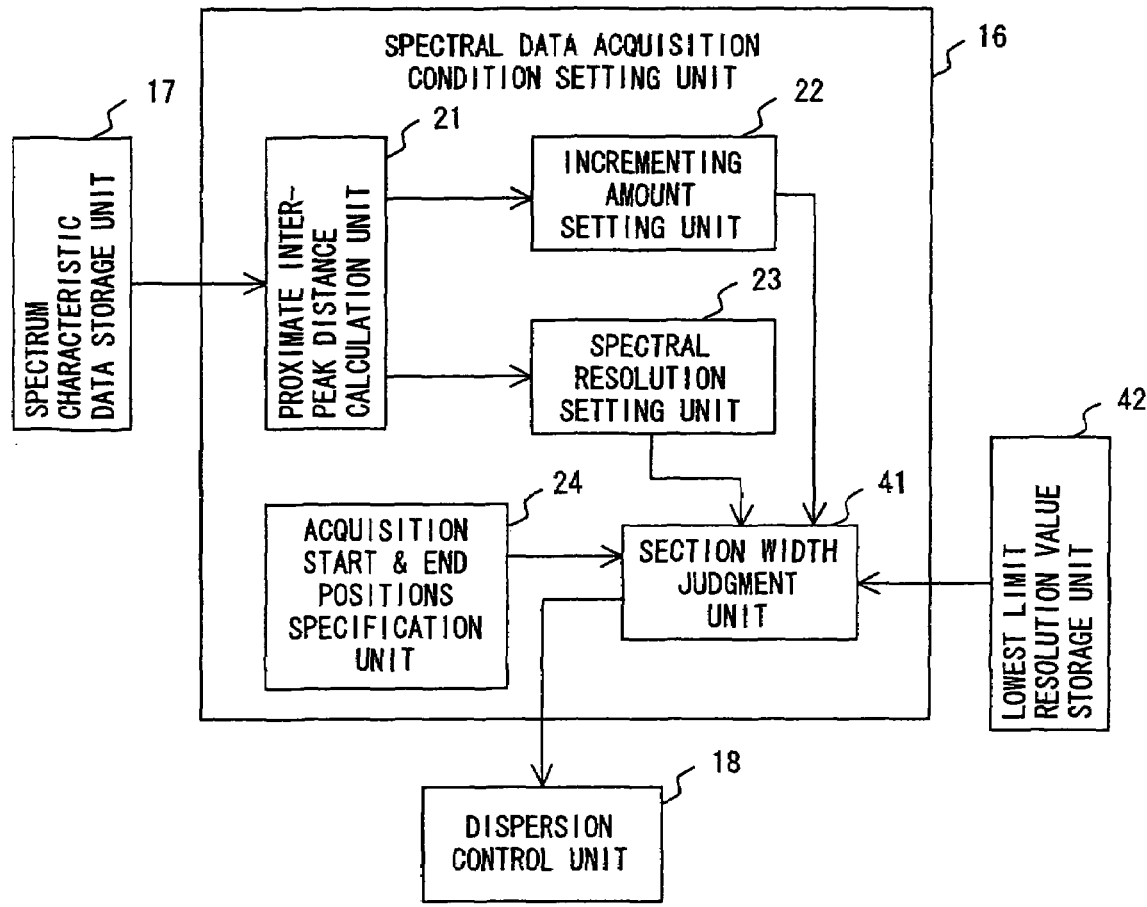
F I G. 17

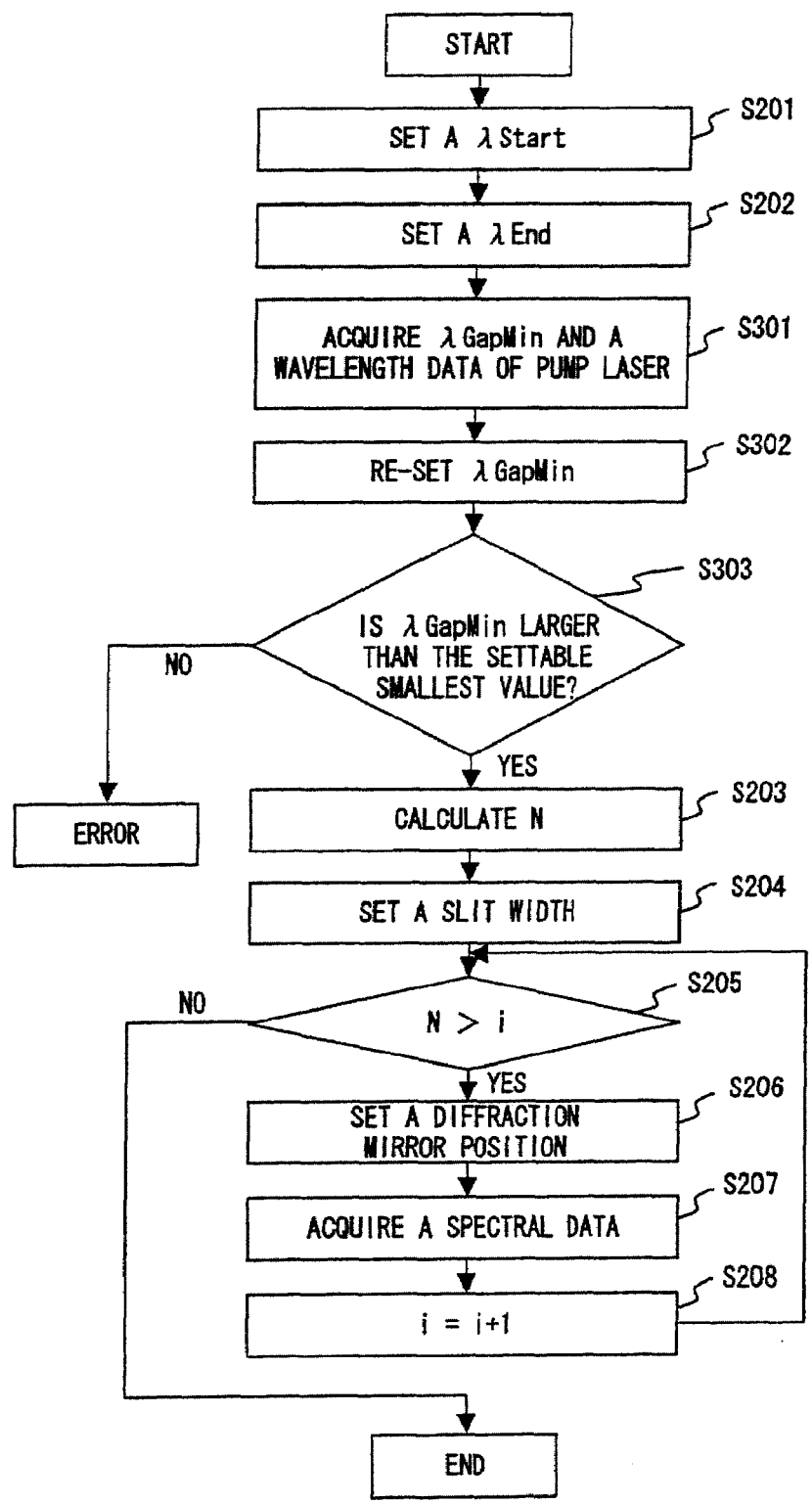
F I G. 19

LASER SCANNING MICROSCOPE, STORAGE MEDIUM STORING SPECTRAL DATA ACQUISITION PROGRAM, AND SPECTRAL DATA ACQUISITION METHOD

CROSS REFERENCE TO RELATED APPLICATIONS

This application is based upon and claims the benefit of priority from the prior Japanese Patent Application No. 2004-217397, filed Jul. 26, 2004, the entire contents of which are incorporated herein by reference.

BACKGROUND OF THE INVENTION

1. Field of the Invention

The present invention relates to a laser scanning microscope for observing a specimen by emitting a laser beam onto the specimen marked with a plurality of fluorescent probes, scanning an observing plane of the specimen in two dimensions, and receiving a fluorescent light from the specimen; and in particular to a spectral data acquisition technique for such a laser scanning microscope.

2. Description of the Related Art

There is a laser scanning microscope which enables an observation by displaying in such as a monitor, through a process of generating an electric signal corresponding to a received fluorescent light back from a specimen by emitting a laser beam onto the specimen marked with a fluorescent probe and creating an image data corresponding to the fluorescent light back from the specimen based on the electric signal.

In order to observe a fluorescent light back from a specimen introduced by a fluorescent probe by using a laser scanning microscope, it is necessary to use a pump laser, photometric dichroic mirror and absorption filter, all of which match with an excitation wavelength and fluorescent peak wavelength of the fluorescent probe.

FIG. 1 is a block diagram showing a configuration of such conventional laser scanning microscope.

As shown by FIG. 1, depending on categories of fluorescent probes for marking a specimen, a plurality of following components, i.e., laser sources 87 through 89 for emitting pump lasers, photometric dichroic mirrors 91 and absorption filters 92, are furnished.

Let it first describe an operation of the laser scanning microscope shown by FIG. 1.

First, the laser sources 87 through 89 emit pump lasers which are focused and synthesized by way of condenser apparatuses 85 and synthesis mirror 86, and which are then emitted onto a specimen (plane) after being transmitted by way of a total reflection mirror 84, excitation dichroic mirror 83, deflection unit 82 and object lens 81.

The fluorescent light back from the specimen corresponding to the emission of pump laser transmits itself by way of the object lens 81 and the deflection unit 82 to reach at the excitation dichroic mirror 83.

The fluorescent light back from the specimen is reflected by the excitation dichroic mirror 83 and converted into electric signals at photoelectric conversion units 93, respectively, after going by way of the photometric dichroic mirror 91, which selects and disperses the fluorescent light from the fluorescent probe, and absorption filters 92 so that a display monitor (not shown herein) displays an image corresponding to the specimen (e.g., cell) as a subject of observation based on the electric signal.

And a selective switching of the combination between the above described photometric dichroic mirror 91 and absorption filter 92 enables a detection of fluorescent light from among the plurality of fluorescent probes.

In the meantime, a patent document noted below has disclosed a technique for automatically setting the optimum combination among an optimal pump laser, photometric dichroic mirror and absorption filter based on a pump laser equipped in a microscope system, spectral data of various filters, excitation wavelength data of fluorescent probes introduced to a test sample (i.e., specimen) and fluorescent wavelength data.

[Patent document 1] Japanese patent laid-open application publication No. 2000-39563: "Method and system configuration for adjusting equipment arrangement for confocal microscope"

SUMMARY OF THE INVENTION

The purpose of the present invention is to provide a laser scanning microscope capable of automatically or semi-automatically setting an acquirable range of spectral data for a specimen in the case of acquiring a fluorescent light from one or a plurality of fluorescent probes for marking the specimen as a continuous data (i.e., $\lambda$ stack data) through measuring by the unit of arbitrary wavelength by continuously changing the photometric wavelength.

In a first aspect of the present invention, a laser scanning microscope, in the one enabling an observation of a specimen through emitting a laser beam onto the specimen marked by a plurality of fluorescent probes and receiving a fluorescent light back from the specimen corresponding to the emission, comprises a laser source for generating a laser beam in an excitation wavelength corresponding to the plurality of fluorescent probes, a deflector unit for scanning the generated laser beam over an observation plane of the specimen, a dispersion unit for dispersing a fluorescent light from the specimen to extract it by an arbitrary wavelength interval, a spectral data acquisition condition setting unit for setting a condition for the dispersion unit acquiring a spectral data based on a spectrum characteristic of the plurality of fluorescent probes, a dispersion control unit for controlling the dispersion unit based on the defined spectral data acquisition condition, and a photoelectric conversion unit for receiving a dispersed fluorescent light to convert into an electrical signal.

In a second aspect of the present invention, vis-à-vis the above described first aspect, a laser scanning microscope further comprises a spectrum characteristic data storage unit for storing a spectrum characteristic of a plurality of fluorescent probes marked for the specimen so that the spectral data acquisition condition setting unit sets a condition for the dispersion unit acquiring a spectral data based on the stored spectrum data.

In a third aspect of the present invention, a laser scanning microscope in the above described first aspect lets the dispersion unit comprise a diffraction mirror for dispersing a fluorescent light back from a specimen into a spectrum and selecting a wavelength, and a slit for selecting a wavelength range of fluorescent light to be received, wherein the spectral data acquisition condition setting unit sets an amount of incrementing of wavelength in relation to a rotation angle of the diffraction mirror and a spectral resolution in relation to width of the slit which are applicable to carrying out a wavelength scanning for the specimen based on a spectrum characteristic of a plurality of fluorescent probes marked for the specimen.

In a fourth aspect of the present invention, a laser scanning microscope in the above described third aspect lets the spectral data acquisition condition definition unit comprise a proximate inter-peak distance calculation unit for calculating the distance between proximate peak wavelengths among a plurality of peak wavelengths based on peak fluorescent wavelengths from the plurality of fluorescent probes, an incrementing amount setting unit for setting a wavelength incrementing amount based on the calculated distance between the proximate peak wavelengths, and a spectral resolution setting unit for setting a spectral resolution based on the calculated distance between proximate peak wavelengths, wherein the dispersion control unit controls the dispersion unit based on the spectral resolution and the wavelength incrementing amount.

In a fifth aspect of the present invention, a laser scanning microscope in the above described fourth aspect lets the spectral data acquisition condition setting unit comprise a section judgment unit for judging whether or not a section is set so as to include two among the peak fluorescent wavelength from each fluorescent probe marked for a specimen and each excitation laser wavelength emitted onto the specimen, wherein the dispersion control unit controls the dispersion unit based on the set section, if it is judged that one among a peak fluorescent wavelength from the each fluorescent probe marked for a specimen and the each excitation laser wavelength emitted onto the specimen is included, or that neither is included.

In a sixth aspect of the present invention, a laser scanning microscope in the above described fifth aspect lets the spectral data acquisition condition definition unit comprise a section division unit for further dividing the set section into a prescribed number if the section is set up so as to include two among the peak fluorescent wavelength from each fluorescent probe marked for a specimen and each said excitation laser wavelength emitted onto the specimen, wherein the section judgment unit judges whether or not the section also set by the section division unit includes two among the peak fluorescent wavelength from each fluorescent probe marked for a specimen and the each excitation laser wavelength emitted onto the specimen.

BRIEF DESCRIPTION OF THE DRAWINGS

FIG. 1 is a block diagram showing a configuration of a conventional laser scanning microscope;

FIG. 2 is a block diagram showing a configuration of a laser scanning microscope according to a first embodiment of the present invention;

FIG. 3 is a block diagram showing a configuration of spectral data acquisition condition setting unit according to the first embodiment;

FIG. 12 is a flow chart showing processing for re-setting the wavelength incrementing amount shown by FIG. 11 in more details;

FIG. 17 is a block diagram with a lowest limit resolution value storage unit and section width judgment unit being added to the block diagram shown by FIG. 3 according to the first embodiment;

FIG. 19 is a flow chart with a processing for comparing a section width with a lowest limit value being added to the one shown by FIG. 11 according to the second embodiment.

DESCRIPTION OF THE PREFERRED EMBODIMENTS

Figure 4:
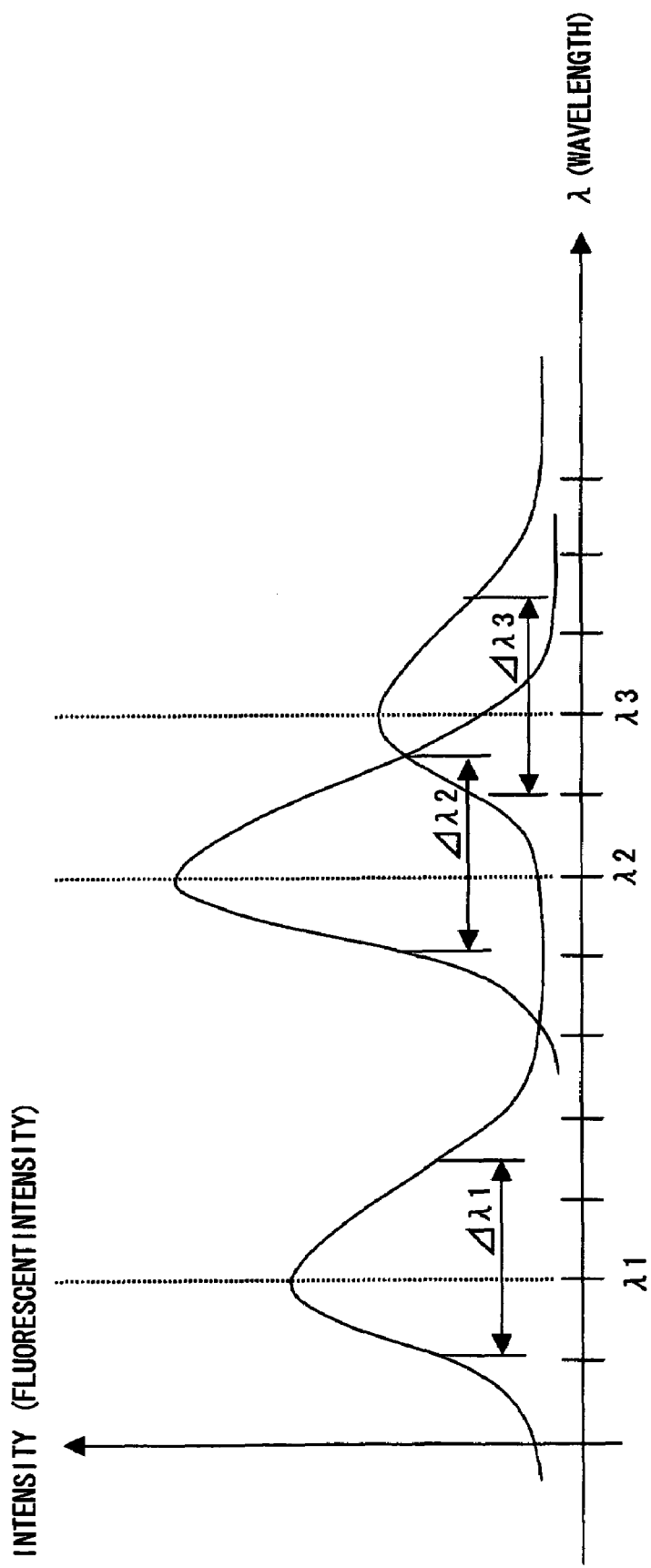
FIG. 4 exemplifies wavelength characteristics of fluorescent lights from respective fluorescent probes in the case of emitting three pump lasers simultaneously onto a specimen marked by the three fluorescent probes.

The present invention makes it possible to lighten a load on an observer who observes a specimen by using a laser scanning microscope.

The present invention also makes it possible to avoid an increase in the number of acquisitions of spectral data unnecessarily within an acquisition range of spectral data.

The following is a detailed description of the preferred embodiment of the present invention while referring to the accompanying drawings.

FIG. 2 is a block diagram showing a configuration of laser scanning microscope according to a first embodiment of the present invention.

In FIG. 2, the laser scanning microscope enables an observation of a specimen through emitting a laser beam onto the specimen marked by a plurality of fluorescent probes and receiving a fluorescent light back from the specimen corresponding to the emission. And as shown by FIG. 2, the laser scanning microscope comprises a laser unit 10 including laser sources 7 through 9 for generating laser beams in excitation wavelengths corresponding to the plurality of fluorescent probes, a deflector unit 2 for scanning the generated laser beam over an observation plane of the specimen, for example, in two-dimensions, a dispersion unit 15 for dispersing a fluorescent light from the specimen by acquiring by an arbitrary wavelength interval, a spectral data acquisition condition setting unit 16 for setting a condition for the dispersion unit 15 acquiring a spectral data, a spectrum characteristic data storage unit 17 for storing known spectrum characteristics of a plurality of fluorescent probes marked for the specimen, such as a peak wavelength of fluorescent light emitted by the each fluorescent probe, a dispersion control unit 18 for controlling the dispersion unit 15 based on the set spectral data acquisition condition, and a photoelectric conversion unit 14 for receiving a dispersed fluorescent light to convert into an electrical signal.

The spectral data acquisition condition setting unit 16, spectrum characteristic data storage unit 17 and dispersion control unit 18 can be comprised as software or hardware in a computer 19 connected with the dispersion unit 15 for example.

As shown by FIG. 2, the dispersion unit 15 comprises a diffraction mirror 13 for dispersing a fluorescent light back from a specimen into a spectrum and selecting a wavelength, and a slit 11 for selecting a wavelength range of fluorescent light to be received so as to be able to acquire an arbitrary fluorescent wave length in an arbitrary wavelength interval by controlling the diffraction mirror 13 and the slit 11 and thereby a λ stack data can easily be obtained.

The spectral data acquisition condition setting unit 16 sets an amount of incrementing wavelength in relation to a rotation angle of the diffraction mirror 13 and a spectral resolution in relation to a width of the slit 11 which are applicable to carrying out a wavelength scanning for the specimen based on the known spectrum characteristics of a plurality of fluorescent probes marked for the specimen.

FIG. 3 is a block diagram showing a configuration of spectral data acquisition condition setting unit 16 according to the first embodiment.

In FIG. 3, the spectral data acquisition condition setting unit 16 comprises a proximate inter-peak distance calculation unit 21 for calculating the distance between proximate peak wavelengths among a plurality of peak wavelengths based on peak fluorescent wavelengths from the plurality of fluorescent probes marked for a specimen, an incrementing amount setting unit 22 for setting the above described amount of incrementing of wavelength based on the calculated distance between proximate peak wavelengths, a spectral resolution setting unit 23 for setting the above described spectral resolution based on the calculated distance between the proximate peak wavelengths, and an acquisition start & end positions specification unit 24 as a user interface capable of specifying acquisition start wavelength and acquisition end wavelength of spectral data.

The dispersion control unit 18 controls the dispersion unit 15, to acquire a spectral data, based on the amount of incrementing of wavelength set by the incrementing amount setting unit 22, spectral resolution set by the spectral resolution setting unit 23 so that the respective borders of adjacent sections (i.e., one acquisition range) are contacting with each other, and acquisition start and end wavelengths of spectral data specified by the user operating the acquisition start & end positions specification unit 24.

Now let it go back to the description about FIG. 2 and about the operation thereof.

First, the laser sources 7 through 9 emit pump lasers which are focused and synthesized by going by way of a condenser apparatus 5 and synthesis mirror 6, and which are then emitted onto a specimen (plane) after being transmitted by way of a total reflection mirror 4, excitation dichroic mirror 3, deflection unit 2 and object lens 1.

The fluorescent light back from the specimen corresponding to the emission of the pump laser transmits itself by way of the object lens 1 and the deflection unit 2 to reach the excitation dichroic mirror 3.

Here, the excitation dichroic mirror 3 is designed in advance so as to transmit a plurality of pump laser beams such as three pump laser beams and reflect a fluorescent light back from the specimen corresponding to the emission of these laser beams onto the specimen.

Because of this, the fluorescent light back from the specimen is dispersed by the excitation dichroic mirror 3, led to a total reflection mirror 12 and thereby further turned, and incident onto the diffraction mirror 13 which is set at a predetermined angle by the dispersion control unit 18.

And the diffraction mirror 13 carries out a spectral factorization of the fluorescent light to select a wavelength.

The slit 11 set at a prescribed width by the dispersion control unit 18 then removes fluorescent light components outside a receiving wavelength range from the fluorescent light coming in from the diffraction mirror 13. The photoelectric conversion unit 14 converts the fluorescent light of the receiving wavelength range into an electric signal, followed by a monitor (not shown herein) displaying an image corresponding to the specimen as a subject of observation (e.g., cell) based on the electric signal.

Here, an angle of the diffraction mirror 13 and width of the slit 11 are both respectively settable by the dispersion control unit 18. For example, a repetition of changing the angle of the diffraction mirror 13 by an increment of prescribed angle and one acquisition of spectral data corresponding to the according width of the slit 11 enables an acquisition of spectral data for a necessary range.

Note here that the present embodiment is configured to enable an observation of corresponding specimen, such as a plurality of observation sites within a cell, by marking the specimen with a plurality of fluorescent probes; in the following description, an operation of the laser scanning microscope according to the present embodiment is explained using sample data.

Note also that, while the present embodiment adopts an apparatus comprising three laser sources 7, 8 and 9 for emitting three pump lasers corresponding to three fluorescent probes, it goes without saying that the number of used fluorescent probes does not always identify with that of the corresponding laser sources and that such corresponding relationship is variable depending on the number of used fluorescent probes and/or the sites in a specimen (e.g., cell) marked thereby, et cetera. For instance, one laser source may correspond to a plurality of fluorescent probes marked for a specimen.

FIG. 4 exemplifies wavelength characteristics of fluorescent lights from respective fluorescent probes in the case of emitting three pump lasers simultaneously onto a specimen marked by the three fluorescent probes.

In FIG. 4, a specimen (e.g., cell) is marked by three fluorescent probes which work on different sites of the cell depending on the type of probe so as to emit a fluorescent light in response to an emission of pump laser thereto, thus enabling an observation thereof. Each of the fluorescent probes is usually configured to emit a fluorescent light of mutually different peak wavelength as shown by FIG. 4 which exemplifies wavelength characteristics relating to three fluorescent probes whose peak wavelength are given by λ1, λ2 and λ3, respectively.

Figure 5A:
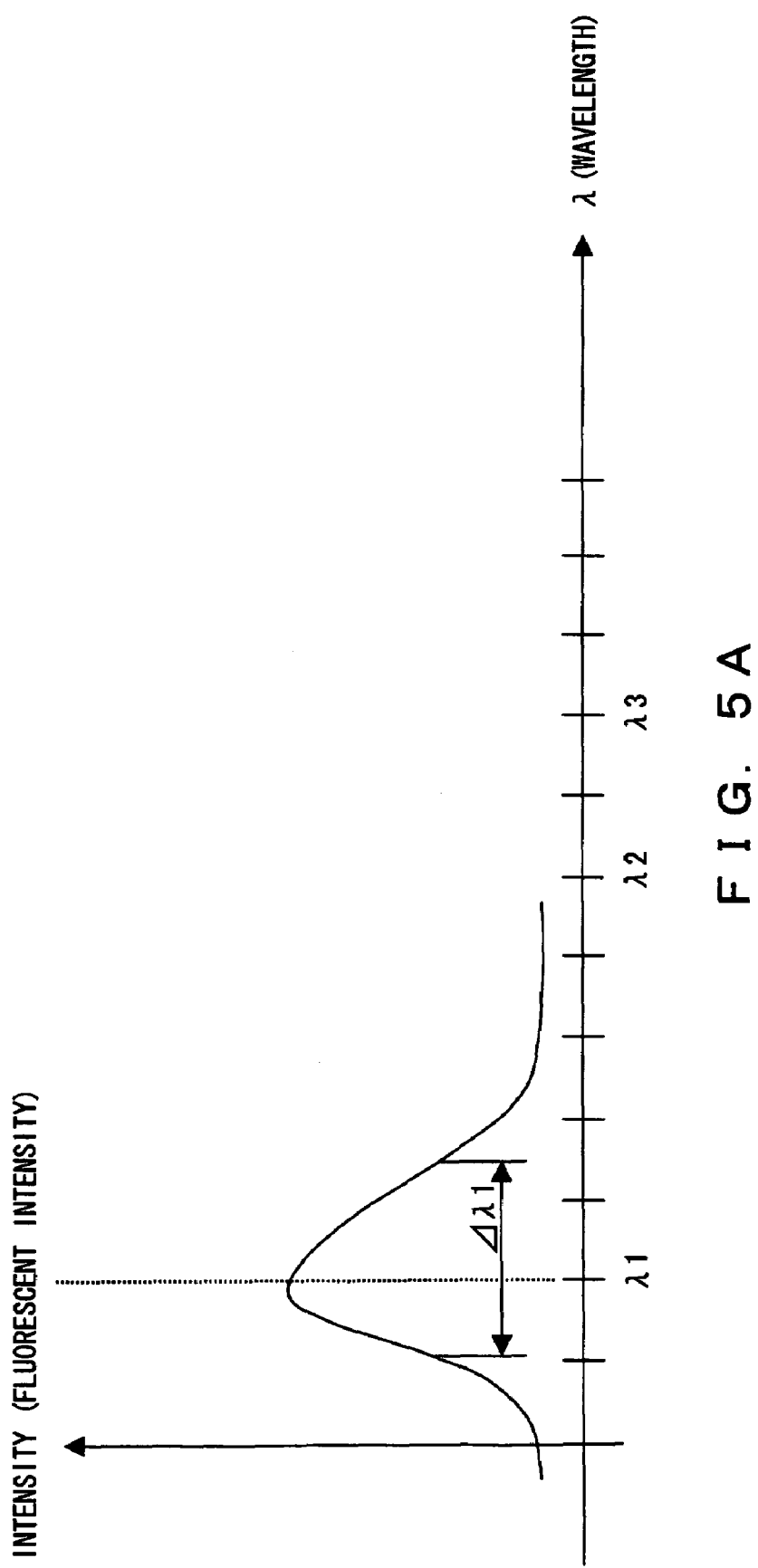
FIG. 5A exemplifies a wavelength characteristic of fluorescent light (peak wavelength: $\lambda 1$) from a fluorescent probe corresponding to a pump laser in the case of emitting either one of three pump lasers at a necessary timing onto a specimen marked by three fluorescent probes.
Figure 5B:
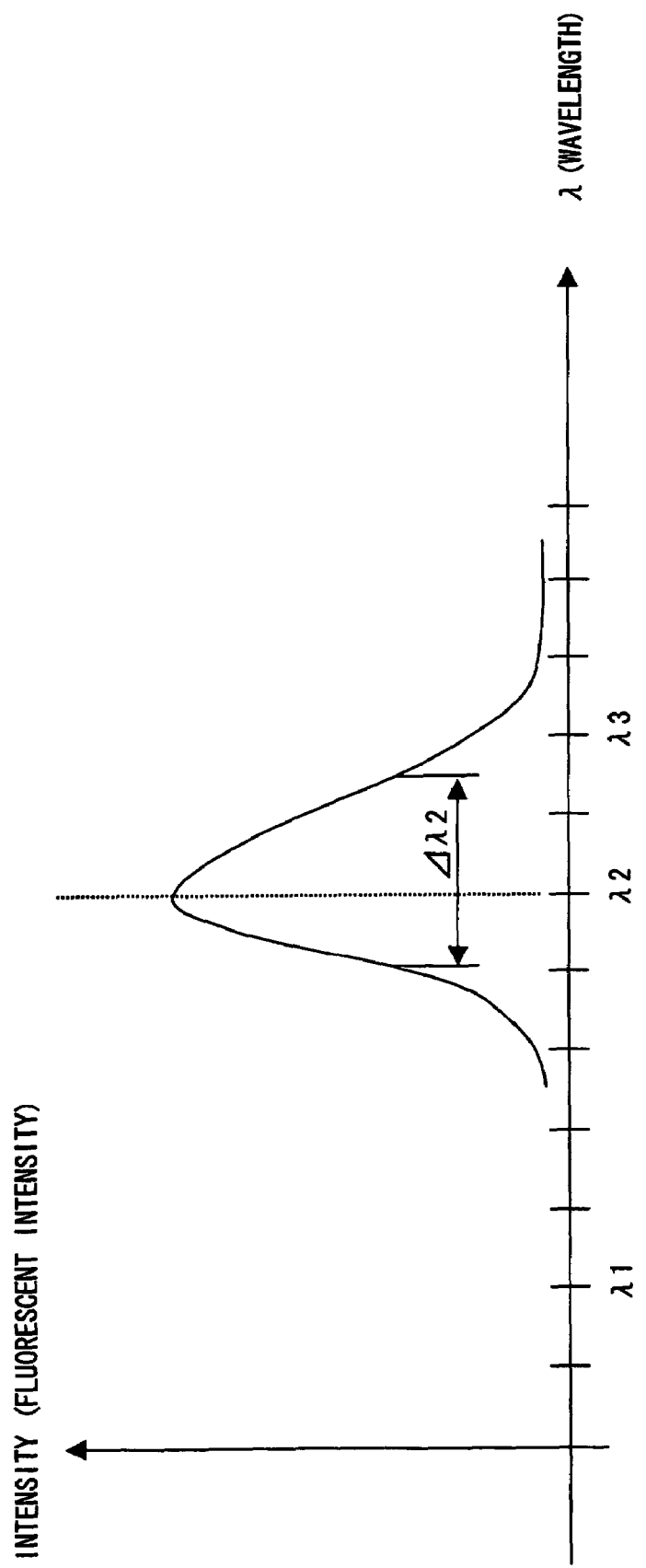
FIG. 5B exemplifies a wavelength characteristic of fluorescent light (peak wavelength: $\lambda 2$) from a fluorescent probe corresponding to a pump laser in the case of emitting either one of three pump lasers at a necessary timing onto a specimen marked by three fluorescent probes.
Figure 5C:
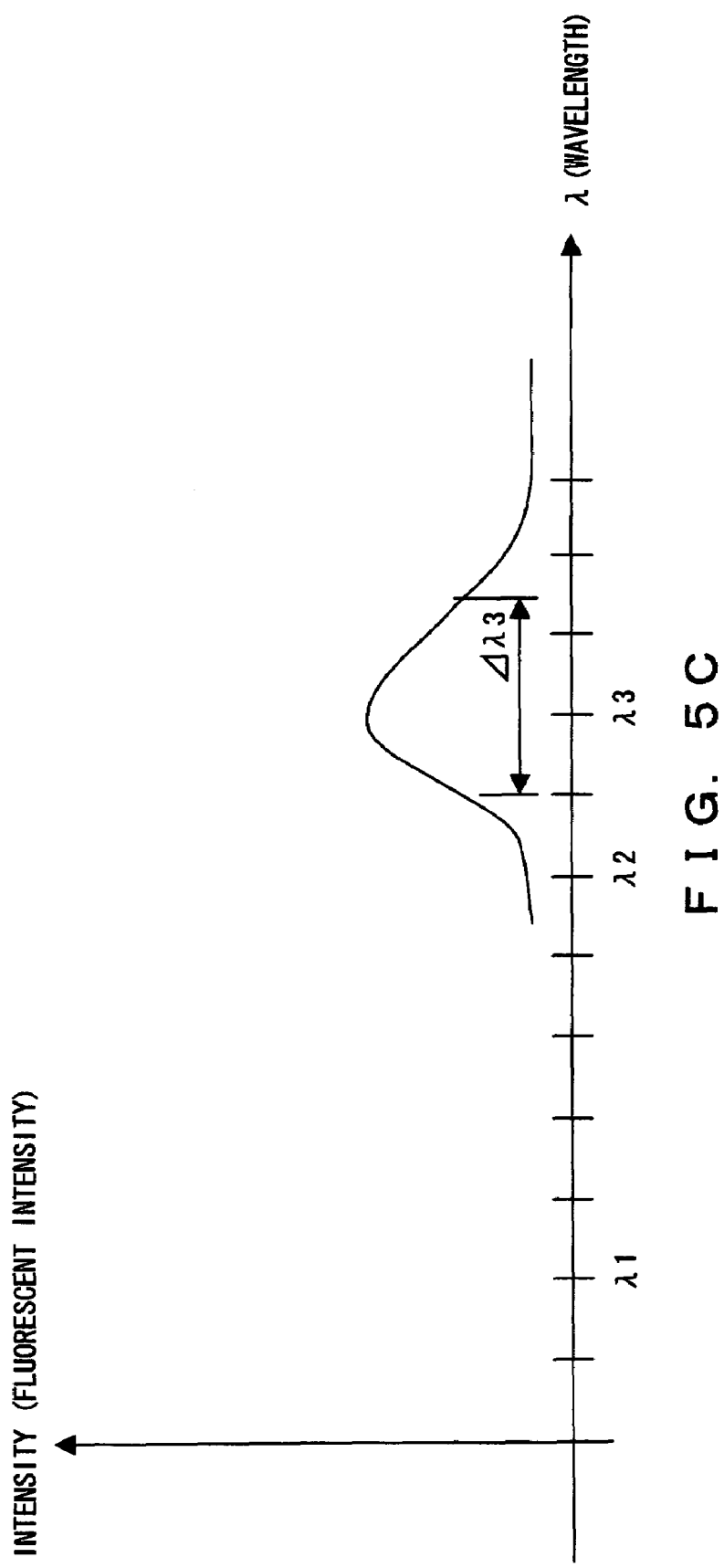
FIG. 5C exemplifies a wavelength characteristic of fluorescent light (peak wavelength: $\lambda 3$) from a fluorescent probe corresponding to a pump laser in the case of emitting either one of three pump lasers at a necessary timing onto a specimen marked by three fluorescent probes.

FIG. 5A through 5C each exemplifies a wavelength characteristic of fluorescent light from a fluorescent probe corresponding to a pump laser in the case of emitting either one of three pump lasers at a necessary timing onto a specimen marked by three fluorescent probes.

That is, FIGS. 5A, 5B and 5C respectively show wavelength characteristics corresponding to the fluorescent probes whose peak wavelength are λ1, λ2 and λ3, respectively.

Incidentally, let it assume that the present embodiment is configured so that the laser sources 7, 8 and 9 emit respective pump lasers corresponding to the fluorescent probes whose peak wavelength are λ1, λ2 and λ3, respectively.

Figure 6:
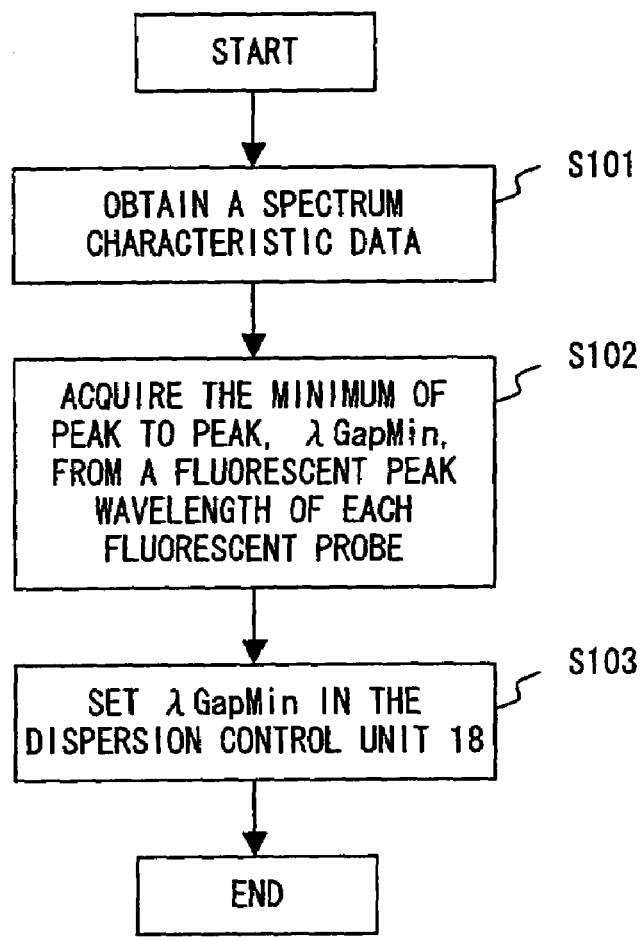
FIG. 6 is a flow chart of processing for setting a wavelength incrementing amount for a dispersion control unit.

FIG. 6 is a flow chart of processing for setting a wavelength incrementing amount for a dispersion control unit. The processing of the flow chart is carried out by the proximate inter-peak distance calculation unit 21 and incrementing amount setting unit 22 shown by FIG. 3.

In FIG. 6, first the proximate inter-peak distance calculation unit 21 obtains, from the spectrum characteristic data storage unit 17, fluorescent peak wavelengths emitted by a plurality of fluorescent probes marked for a specimen (step S101) (simply "S101" hereinafter). Here, the assumption is that the following values are stored by the spectrum characteristic data storage unit 17 as the fluorescent peak wavelengths emitted by the respective fluorescent probes for example:

λ1=510 nm

λ2=560 nm

λ3=580 nm

Then, the proximate inter-peak distance calculation unit 21 acquires the difference in proximate peak wavelengths from the acquired peak wavelengths λ1, λ2 and λ3 to store in a variance λGapMin (S102). In this example, the difference between the λ2 and λ3 is the minimum and therefore the λGapMin is calculated as follows:

λGapMin=|λ2−λ3|=|560−580|=20 nm

Then, the incrementing amount setting unit 22 sets the value of the λGapMin for the dispersion control unit 18 as the rotation angle of the diffraction mirror (i.e., wavelength incrementing amount) (S103), such as a rotation angle of 0.5 degrees for a wavelength incrementing amount of 20 nm if one (1) degree corresponds to 40 nm of incrementing amount.

Through such processing, the incrementing amount setting unit 22 sets the amount of incrementing of wavelength to be identified with a proximate inter-peak distance, so it is possible to avoid plurality of fluorescent peaks being included within an acquisition section of one spectral data and it is possible to avoid increase in the number of unnecessary acquisitions of spectral data within an acquisition range thereof. The number of acquisitions can be increased, for example, by trying not to include a plurality of fluorescent peaks in the acquisition section of one spectral data.

Also, it is possible for the dispersion control unit 18 to acquire an arbitrary fluorescent wavelength by an arbitrary wavelength interval, and accordingly a λ stack data, through controlling the dispersion unit. The spectral data acquisition condition setting unit 16 is also enabled to define a condition for the dispersion unit acquiring a spectral data based on the known spectrum characteristics of a plurality of fluorescent probes marked for a specimen, thus making it possible to set the range of acquiring a valid spectral data automatically or semi-automatically for a sample (i.e., specimen) introduced by a plurality of fluorescent probes. This in turn makes it possible to lighten a load on the observer who observes a specimen by using a laser scanning microscope.

Figure 7:
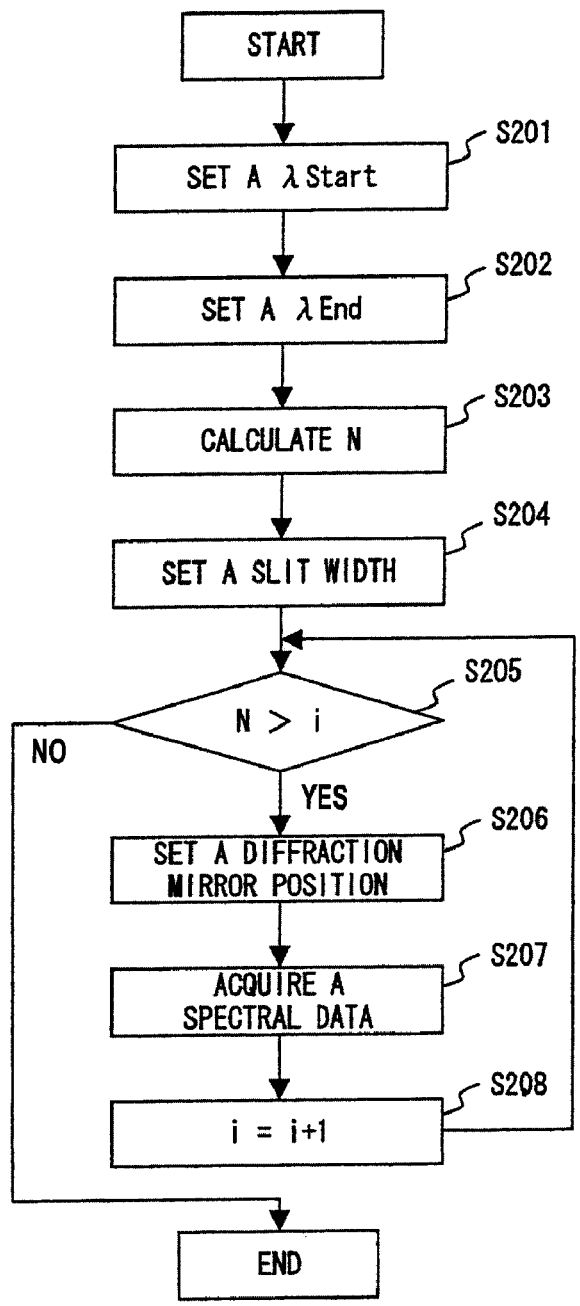
FIG. 7 is a flow chart of processing for acquiring a spectral data by controlling a dispersion unit according to the first embodiment.

FIG. 7 is a flow chart of processing for acquiring a spectral data by controlling a dispersion unit according to the first embodiment. The spectral resolution setting unit 23 and dispersion control unit 18, et cetera, shown by FIG. 3 carry out the processing of the flow chart.

In FIG. 7, first the user specifies an acquisition start wavelength, λStart, of spectral data by operating the acquisition start & end positions specification unit 24 (S201); and specifies an acquisition end wavelength, λEnd, by likewise operating the acquisition start & end positions specification unit 24 (S202).

Then, the dispersion control unit 18 divides the acquisition range defined by the acquisition start and end wavelengths by the already set wavelength incrementing amount, thereby calculating the number of acquisitions (i.e., the number of repetitions of the acquisitions) N of one spectral data which is required for acquiring a spectral data for the acquisition range, by the following expression (S203):

N=(λEnd−λStart)/λGapMin

Then, the spectral resolution setting unit 23 sets a slit width (i.e., spectral resolution), λResolution, based on the above calculated λGapMin (S204). In this step the slit width λResolution is set so as to identify with the λGapMin (i.e., λResolution=λGapMin), that is, the borders of the adjacent acquisition ranges of one acquisition are in contact with each other.

Then, a spectral data of one acquisition will be acquired in sequence by repeating the ensuing loop processing in the steps S205 through S208.

Before starting the loop processing, a counter I is initialized as "0", followed by judging whether or not the already calculated number of repetition N is larger than the counter I (i.e., N>I) (S205).

If the N is equal to, or smaller than, I in the step S205, the series of processing ends.

If the N is larger than I in the step S205, proceed to the step S206, in which the dispersion control unit 18 rotates the diffraction mirror to the following position:

λStart+(I*λGapMin)

Then carry out an acquisition processing of one acquisition of spectral data (S207), that is, as described above, the pump laser emitted by the laser sources 7 through 9, followed by being condensed and synthesized, is bi-dimensionally scanned (i.e., emitted) on the specimen (plane) so that a fluorescent light back from the specimen corresponding to the emission goes by way of the object lens 1, deflector unit 2, excitation dichroic mirror 3 to arrive at the total reflection mirror 12, to be turned thereby, then to be incident on the diffraction mirror 13 which has been angled (i.e., positioned) by the dispersion control unit 18 in the step S206. Then the diffraction mirror 13 carries out a spectrum factorization of the fluorescent light and a wavelength selection. Furthermore, the dispersion control unit 18 removes a fluorescent component outside the receiving wavelength range from the incident fluorescent light by way of the diffraction mirror 13 using the slit 11 where its width is set in step S204. The photoelectric conversion unit 14 converts the fluorescent light within the receiving wavelength range, which passed through the slit 11, into an electric signal. Such is how one acquisition of spectral data is acquired.

Then, increments the counter variable I by one ("1") followed by returning to the step S205 (S208), in which the incremented counter I will be compared with the number of repetition N.

Figure 8:
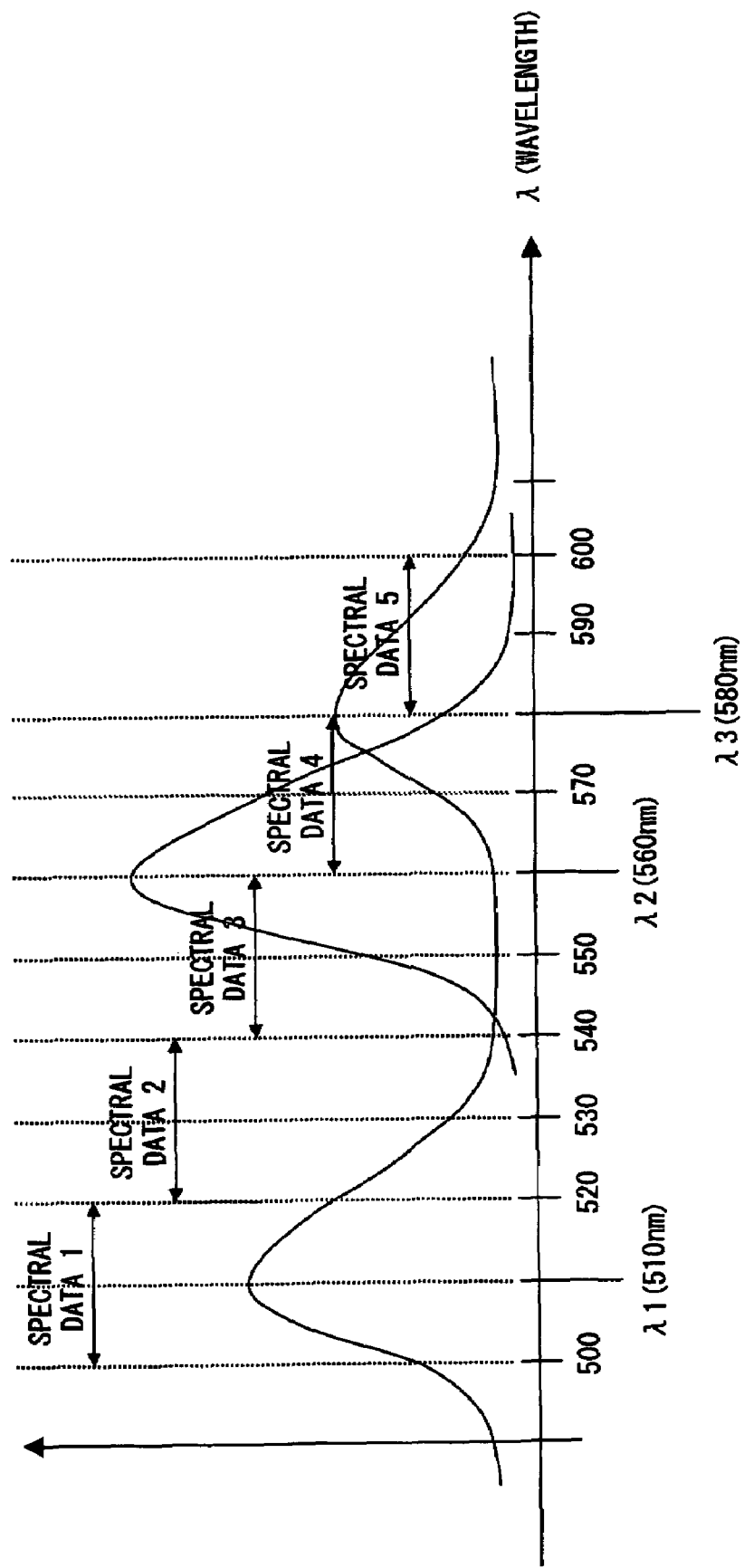
FIG. 8 exemplifies an acquisition range of spectral data set in relation to a wavelength characteristic of fluorescent light from the three fluorescent probes shown by FIG. 4 (No 1)

FIG. 8 exemplifies an acquisition range of spectral data set in relation to a wavelength characteristic of fluorescent light from the three fluorescent probes shown by FIG. 4 (No 1).

In FIG. 8, the user operates the acquisition start & end positions specification unit to specify an acquisition start wavelength $\lambda$Start and acquisition end wavelength $\lambda$End of spectral data as follows:

$\lambda$Start=500 nm $\lambda$End=600 nm

Since the proximate inter-peak distance $\lambda$ GapMin is given by 20 nm as described above, one acquisition of spectral data will be done through five intervals in this example as follows: 500 to 520 nm, 520 to 540 nm, 540 to 560 nm, 560 to 580 nm and 580 to 600 nm.

Note that, if the acquired spectral data includes a fluorescent peak wavelength and a peak wavelength of pump laser corresponding to the peak wavelength, it is actually difficult to observe a site within a specimen (e.g., cell) corresponding to the peak wavelength among the acquired spectral data, but such an acquisition range may be discarded, instead of using it, in the actual usage. Therefore, a setting method for acquisition range with no consideration of wavelength position of the pump laser, as with the above described first embodiment, is also useful. In a second embodiment to be described in the following, an acquisition range is set in consideration of such wavelength position of a pump laser.

Incidentally, the second embodiment also adopts basically the configuration of the laser scanning microscope shown by FIG. 2.

Figure 9:
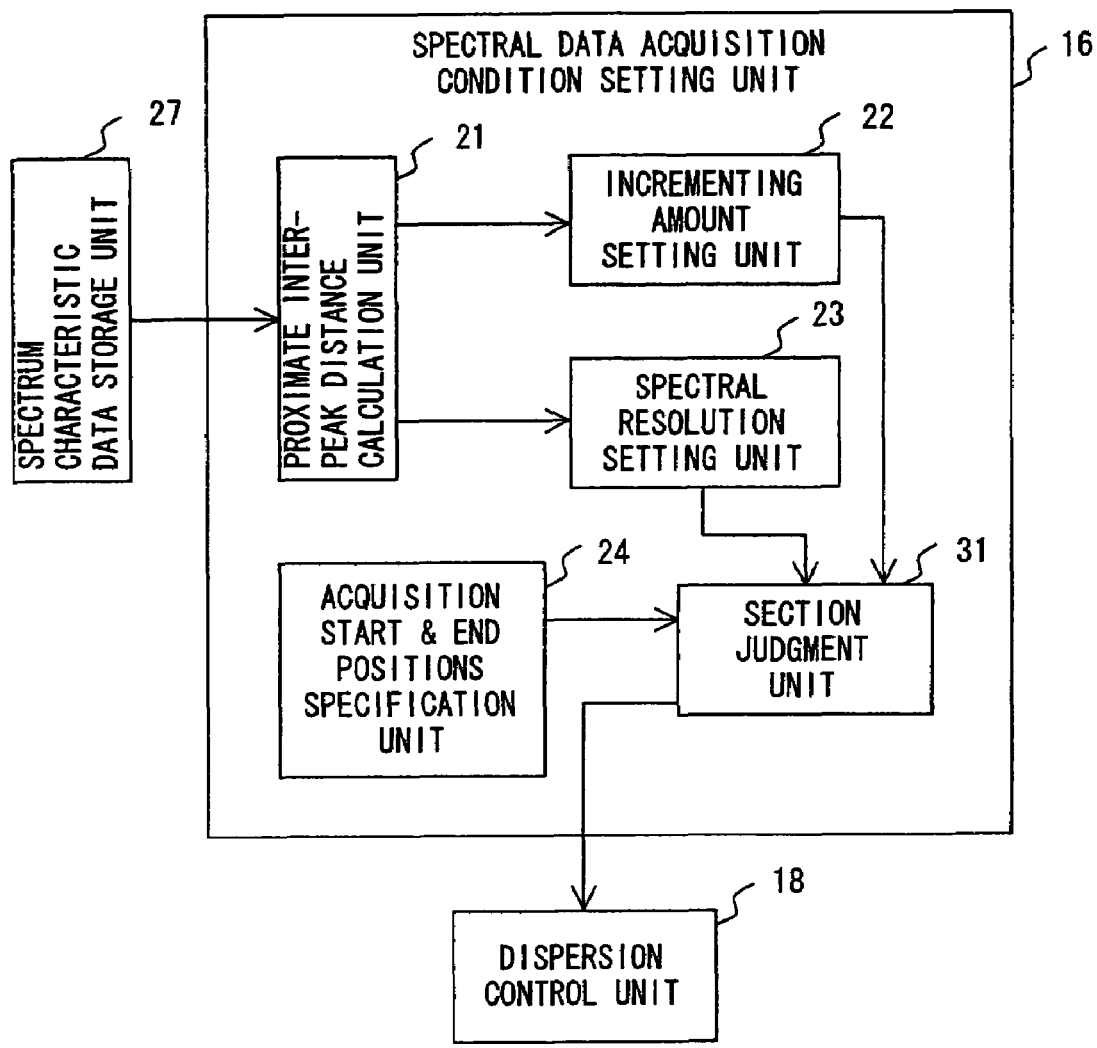
FIG. 9 is a block diagram showing a configuration of spectral data acquisition condition setting unit according to a second embodiment.

FIG. 9 is a block diagram showing a configuration of the spectral data acquisition condition setting unit 16 according to the second embodiment.

In FIG. 9, vis-à-vis FIG. 3, the spectral data acquisition condition setting unit 16 comprises a section judgment unit 31 for judging whether or not a section is set so as to include two among a peak wavelength of fluorescent light from each fluorescent probe marked for a specimen and each pump laser wavelength emitted onto the specimen. And if the section judgment unit 31 judges that the section includes one among a peak wavelength of fluorescent light from the each fluorescent probe marked for a specimen and the each pump laser wavelength emitted onto the specimen, or that the section includes neither, then the dispersion control unit 18 acquires a spectral data by controlling the dispersion unit based on the set section.

Incidentally, a section division unit may be comprised for dividing the section if the condition defined by the section judgment unit 31 is not satisfied.

Figure 10:
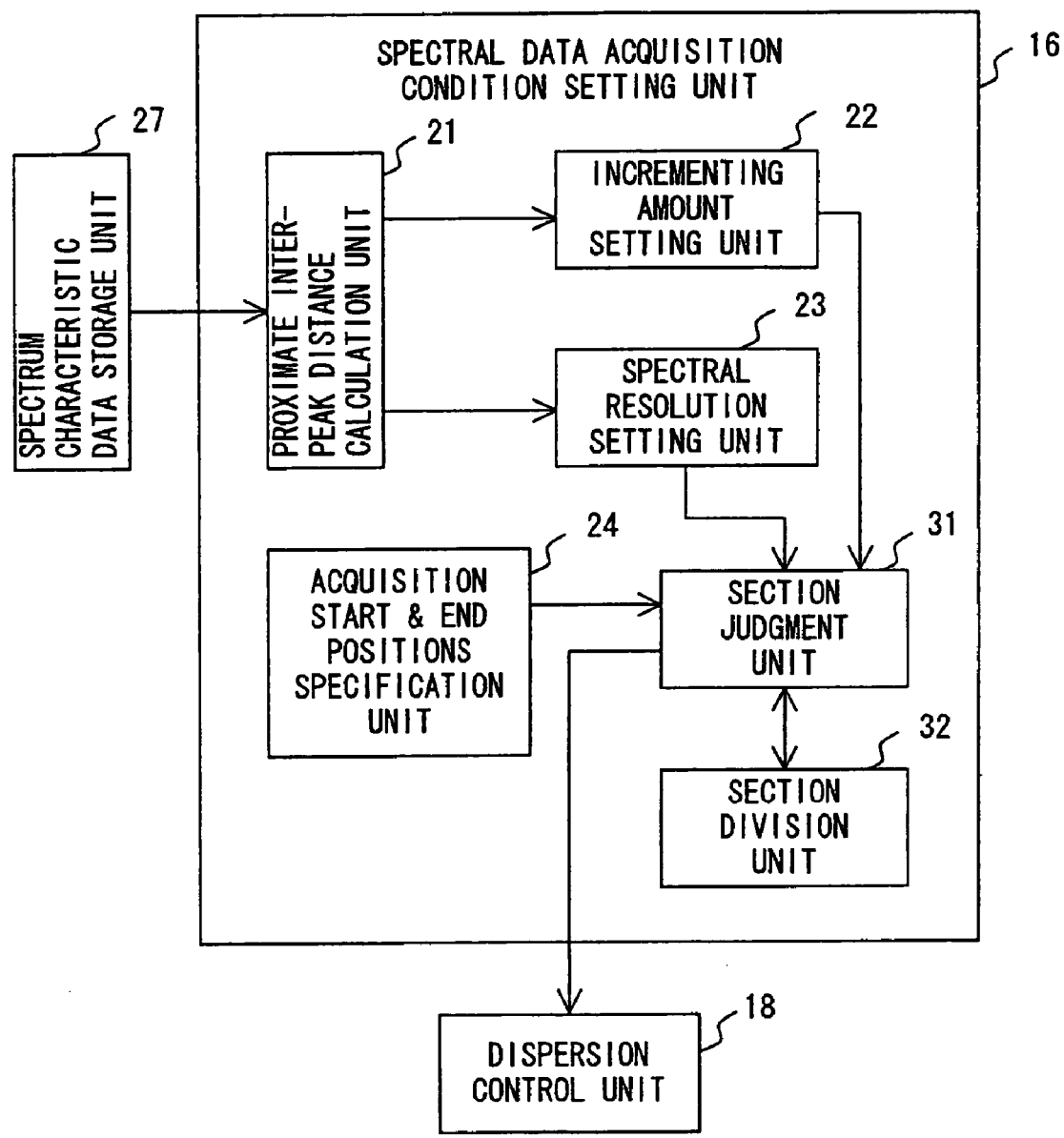
FIG. 10 is a block diagram showing a variation of spectral data acquisition condition setting unit according to the second embodiment.

FIG. 10 is a block diagram showing a variation of the spectral data acquisition condition setting unit 16 according to the second embodiment.

In FIG. 10, vis-à-vis FIG. 9, the spectral data acquisition condition setting unit 16 further comprises a section division unit 32 for dividing a set section further into a prescribed number of sections if the section judgment unit 31 judges that the section is set so as to include two among a peak wavelength of fluorescent light from each fluorescent probe marked for a specimen and each pump laser wavelength emitted onto the specimen. And the section judgment unit 31 judges also for a section divided by the section division unit 32 as to whether or not the section is set so as to include two among a peak wavelength of fluorescent light from each fluorescent probe marked for a specimen and each pump laser wavelength emitted onto the specimen.

Such configuration makes it possible to set a section satisfying the condition set forth by the section judgment unit 31 through a repetition of dividing by using the section division unit 32.

Meanwhile, in the present second embodiment, a spectrum characteristic data storage unit 27 stores peak wavelengths of respective fluorescent probes and pump laser wavelengths corresponding to the respective peak wavelengths by correlating with one another. For example, if three fluorescent probes are used for marking a specimen, with the fluorescent peak wavelengths of the respective fluorescent probes being $\lambda$1 (=510 nm), $\lambda$2 (=560 nm) and $\lambda$3 (=580 nm), and with the pump laser wavelength corresponding to the respective fluorescent peak wavelengths being Ex$\lambda$1 (=492 nm), Ex$\lambda$2 (=542 nm) and Ex$\lambda$3 (=575 nm), then the spectrum characteristic data storage unit 27 stores the data as follows:

$\lambda$1=510 nm Ex$\lambda$1=492 nm $\lambda$2=560 nm Ex$\lambda$2=542 nm $\lambda$3=580 nm Ex$\lambda$3=575 nm The following description is about an operation of the laser scanning microscope according to the second embodiment. First, through the same processing as the flow chart shown by FIG. 6 of the first embodiment, the proximate inter-peak distance calculation unit 21 sets the distance between proximate peak wavelengths set for a variable $\lambda$GapMin, and the incrementing amount setting unit 22 sets the distance between proximate peak wavelengths as a wavelength incrementing amount in the dispersion control unit.

Figure 11:
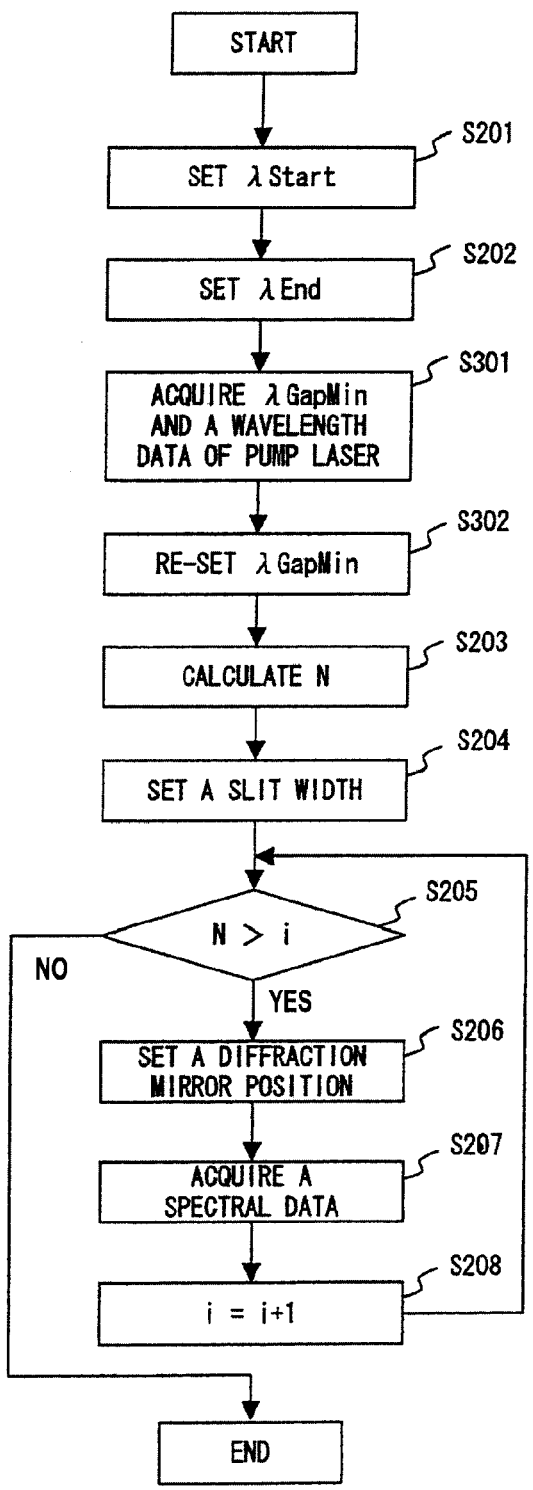
FIG. 11 is a flow chart of processing for acquiring a spectral data by controlling a dispersion unit according to the second embodiment.

FIG. 11 is a flow chart of processing for acquiring a spectral data by controlling a dispersion unit according to the second embodiment. The spectral resolution setting unit 23, section judgment unit 31, and dispersion unit 18, et cetera, shown by FIG. 9 or 10 carry out the processing of the flow chart.

The flow chart shown by FIG. 11 has actually added the processing of steps S301 and S302 to the flow chart shown by FIG. 7.

The added step S301 is to obtain a set $\lambda$GapMin, and pump laser wavelengths Ex$\lambda$1, Ex$\lambda$2 and Ex$\lambda$3, all of which are stored by the spectrum characteristic data storage unit 27. And the step S302 is to carry out the processing of re-setting the once set wavelength incrementing amount, such as dividing it into a prescribed number, by referring to the obtained $\lambda$GapMin and each wavelength of pump laser by the processing of step S301.

FIG. 12 is a flow chart showing the processing of the step S302 (for re-setting the wavelength incrementing amount) shown by FIG. 11 in more details.

In FIG. 12, first initialize the counter value at "0" (S401). Then calculate a spectral data acquisition start wavelength λSectionStart (=λStart+I*λGapMin) of the current (i.e., I-th number) section based on the already set acquisition start wavelength λStart and λGapMin and judges whether or not the spectral data acquisition start wavelength λSectionStart of the current section is smaller than the already set acquisition end wavelength λEnd (S402).

If the spectral data acquisition start wavelength λSectionStart of the current section is judged to be equal to or greater than the λEnd in the step S402, the series of processing ends.

On the other hand, if the spectral data acquisition start wavelength λSectionStart of the current section is judged to be smaller than the λEnd in the step S402, proceed to the step S403 which calculates a spectral data acquisition end wavelength λSectionEnd (=λStart+(I+1)*λGapMin) of the current section. As is usually the case, the spectral data acquisition end wavelength of the current section identifies with a spectral data acquisition start wavelength of the next section.

Then judges whether or not two among the peak wavelengths Exλ1, Exλ2 and Exλ3 of the respective pump lasers emitted onto a specimen and fluorescent peak wavelengths λ1, λ2 and λ3 from the respective fluorescent probes marked for the specimen, all of which are stored by the spectrum characteristic data storage unit 17, are included in the current section, that is, between the λSectionStart and λSectionEnd (S404).

If two among the Exλ1, Exλ2, Exλ3, λ1, λ2 and λ3 are judged to be included between the λSectionStart and λSectionEnd in the step S404, the value of the λGapMin is re-set (i.e., divided) at a half (i.e., λGapMin=λGapMin/2) (S405), followed by returning to the step S401 for repeating the above described processing.

On the other hand, if one among the Exλ1, Exλ2, Exλ3, λ1, λ2 and λ3 is judged to be included, or either is judged not to be included, between the λSectionStart and λSectionEnd in the step S404, the counter I is incremented by one (i.e., I=I+1) (S406), followed by returning to S402 for carrying out the processing for the step S402 and thereafter.

Then the processing of the step S203 shown by FIG. 11 and thereafter will be carried out based on the section set as described above.

Figure 13:
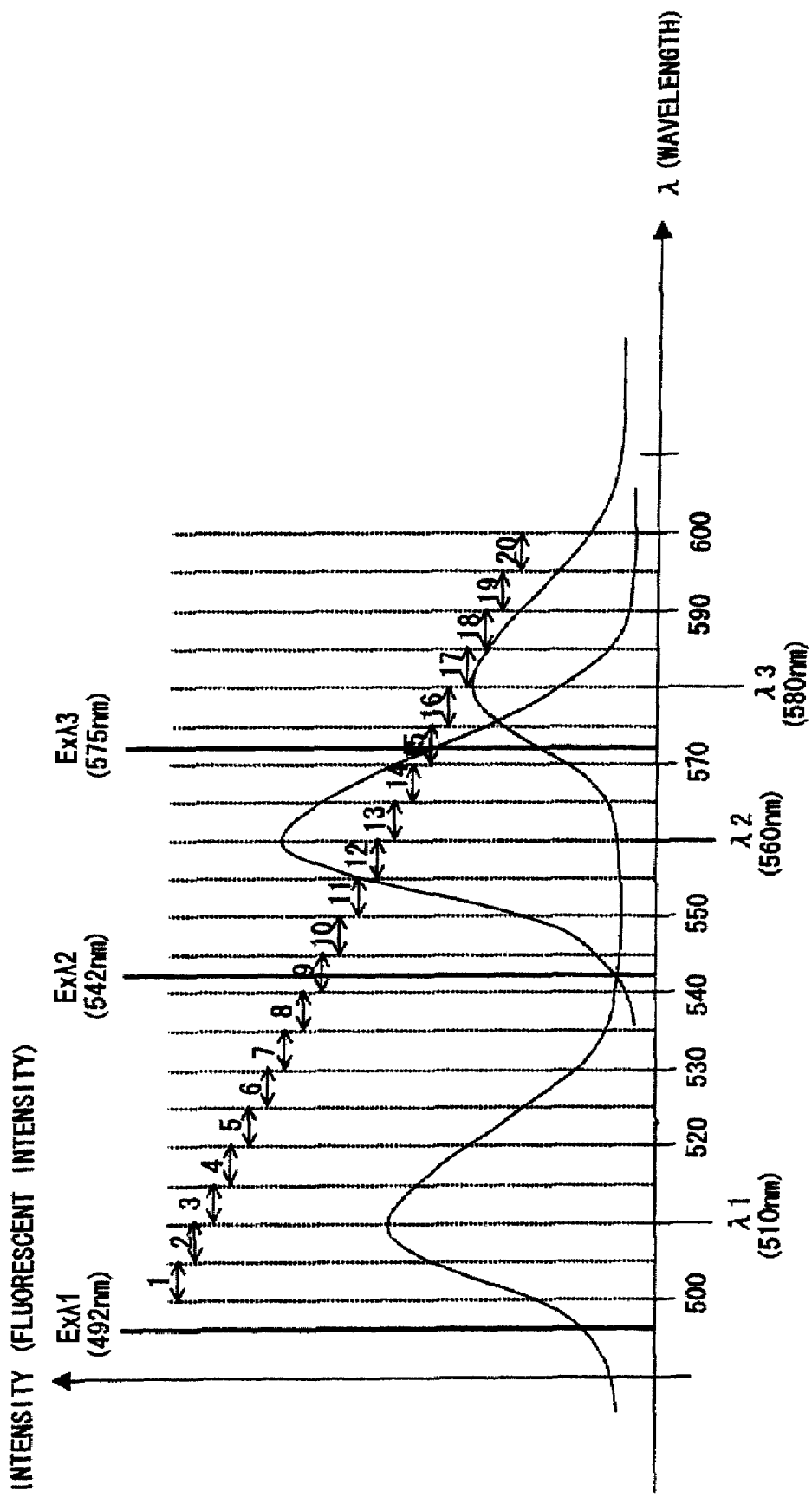
FIG. 13 exemplifies an acquisition range of spectral data set in relation to a wavelength characteristic of fluorescent light from the three fluorescent probes shown by FIG. 4 (No 2)

FIG. 13 exemplifies an acquisition range of spectral data set in relation to a wavelength characteristic of fluorescent light from the three fluorescent probes shown by FIG. 4 (No 2).

In FIG. 13, the user operates the acquisition start & end positions specification unit to specify an acquisition start wavelength λStart and acquisition end wavelength λEnd as follows:

λStart=500 nm

λEnd=600 nm

Since the proximate inter-peak distance λGapMin is given by 20 nm, the acquisition of spectral data has initially been supposed to be carried out in five times in the increment of 500 to 520 nm, 520 to 540 nm, 540 to 560 nm, and 580 to 600 nm.

However, since a pump laser peak wavelength Exλ3 (=575 nm) and a fluorescent peak wavelength λ3 (=580 nm) are included in a section 560 to 580 nm, for instance, in the width of initial section (20 nm), two among the Exλ1, Exλ2, Exλ3, λ1, λ2 and λ3 are judged to be included between the λSectionStart (=560 nm) and λSectionEnd (=580 nm) in the case of the current section being a section, 560 to 580 nm, in the step S404 shown by FIG. 12 and consequently the value of λGapMin will be re-set (i.e., divided) at 10 nm, i.e., a half of 20 nm, in the ensuing step S405.

However, even with the re-setting, resulting in being divided to 10 sections, i.e., 500 to 510 nm—and so on—590 to 600 nm, a pump laser peak wavelength Exλ3 (=575 nm) and fluorescent peak wavelength λ3 (=580 nm) are included in the section, 570 to 580 nm, and therefore two among the Exλ1, Exλ2, Exλ3, λ1, λ2 and λ3 are judged to be included between the λSectionStart (=570 nm) and λSectionEnd (=580 nm) in the case of the current section being a section, 570 to 580 nm, in the step S404 shown by FIG. 12 and consequently the value of λGapMin will be re-set (i.e., divided) at 5 nm, a half of 10 nm, in the ensuing step S405.

Then, as a result, divided to 20 sections, i.e., 500 to 505 nm—and so on—595 to 600 nm and one among the Exλ1, Exλ2, Exλ3, λ1, λ2 and λ3 is then judged to be included, or either is judged not to be included, between the λSectionStart and λSectionEnd for either section in the step S404 shown by FIG. 12, and therefore the dispersion control unit will obtain a spectral data by controlling the dispersion unit based on this section.

In the above description, the user operates the acquisition start & end positions specification unit 24 shown by FIGS. 3, 9, and 10 to specify an acquisition start and end wavelengths of the spectral data, the acquisition start and end wavelengths, that is, an acquisition range, can be specified automatically. A third embodiment to be described below specifies an acquisition range automatically.

The third embodiment also adopts basically a configuration of laser scanning microscope shown by FIG. 2.

Figure 14:
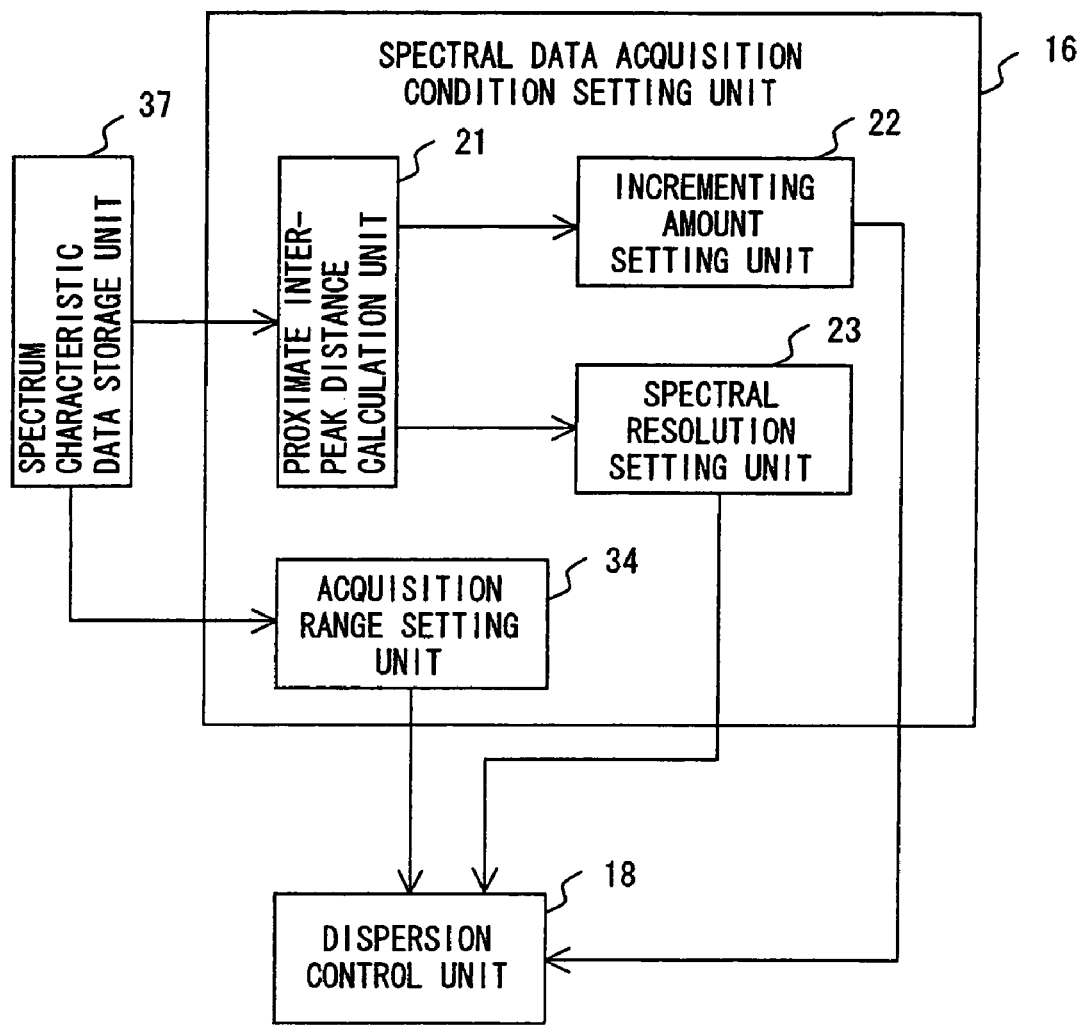
FIG. 14 is a block diagram showing a configuration of spectral data acquisition condition setting unit according to a third embodiment.

FIG. 14 is a block diagram showing a configuration of spectral data acquisition condition setting unit 16 according to the third embodiment.

The spectral data acquisition condition setting unit 16 shown by FIG. 14, vis-à-vis FIG. 3, comprises an acquisition range setting unit 34 in place of the acquisition start & end positions specification unit 24. The acquisition range setting unit 34 sets an acquisition start and end wavelengths of spectral data based on the known spectrum characteristics, stored by a spectrum characteristic data storage unit 37, of a plurality of fluorescent probes marked for a specimen.

The acquisition range setting unit 34 sets an acquisition range of spectral data so as to include all the peak wavelengths corresponding to all fluorescent probes marked for the specimen, and, in this event, sets a wavelength position being moved toward an edge where a value of distribution curve corresponding to a right most or left most peak wavelengths decreases by a prescribed ratio from its peak as an acquisition start or end positions for a spectral data.

In the third embodiment, the spectrum characteristic data storage unit 37 stores a peak wavelength of each fluorescent probe and its half-value section (i.e., a displacement from a peak wavelength to a wavelength position where a value of the distribution curve decreases to a half of the peak value), with the aforementioned two being related with each other.

Figure 15:
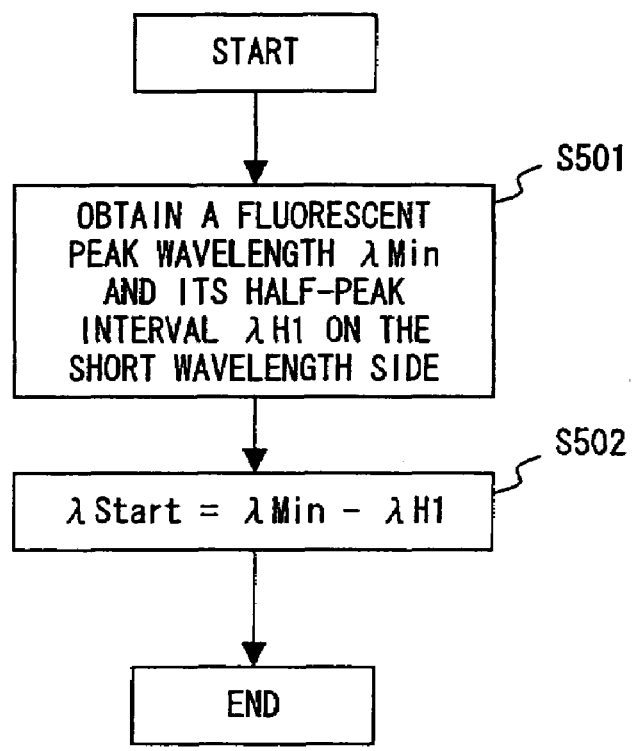
FIG. 15 is a flow chart of processing for setting an acquisition start wavelength of spectral data.
Figure 16:
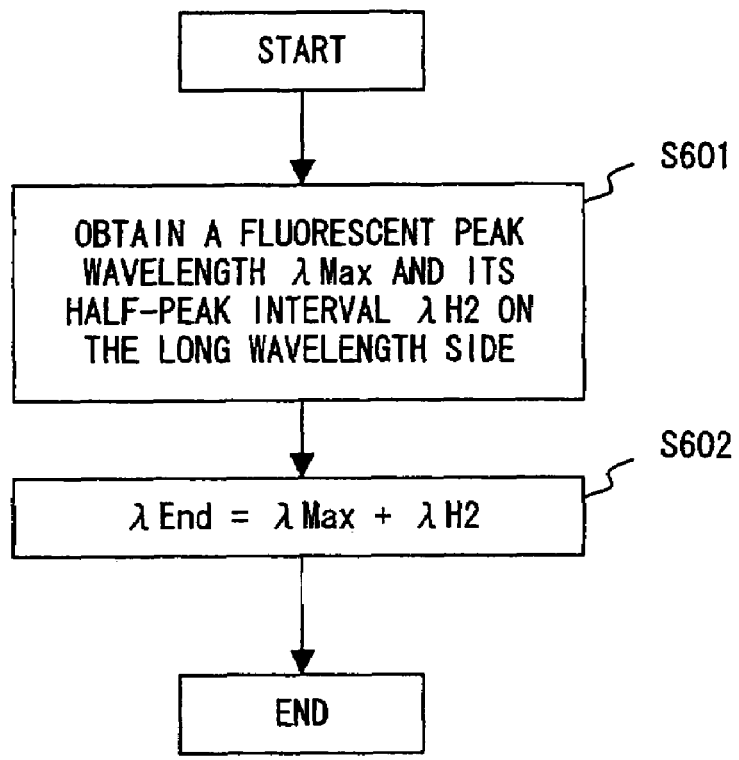
FIG. 16 is a flow diagram of processing for setting an acquisition end wavelength of spectral data.

For example, in the case of three fluorescent probes marking a specimen, with the peak wavelength of each fluorescent probe being λ1 (=510 nm), λ2 (=560 nm) and λ3 (=580 nm), and the half-value sections corresponding to the respective peak wavelengths being Δλ1 (=±20 nm), Δλ2 (=±15 nm) and Δλ3 (=±10 nm), then the spectrum characteristic data storage unit 37 stores the data as follows:

$\lambda 1 = 510$ nm $\Delta\lambda 1 = \pm 20$ nm $\lambda 2 = 560$ nm $\Delta\lambda 2 = \pm 15$ nm $\lambda 3 = 580$ nm $\Delta\lambda 3 = \pm 10$ nm The following description is about an operation of the laser scanning microscope according to the third embodiment while referring to the flow chart shown by FIGS. 15 and 16.

FIG. 15 is a flow chart of processing for setting an acquisition start wavelength of spectral data. The processing as per the flow chart is carried out by the acquisition range setting unit 34 shown by FIG. 14.

In FIG. 15, the acquisition range setting unit 34 first obtains a peak wavelength ($\lambda 1$ in this case) of the fluorescent light in the shortest wavelength range (i.e., left side) out of the spectrum characteristic data storage unit 37 to set it for a variable $\lambda$Min; and likewise obtains its half-peak interval (i.e., a displacement from the peak wavelength; $\Delta\lambda 1$ in this case) to set it for a variable $\lambda$H1 (S501).

Then the acquisition range setting unit 34 acquires an acquisition start position $\lambda$ Start for a spectral data based on the following expression (S502):

$$\lambda Start = \lambda Min - \lambda H1$$

Here in the step S502, the displacement amount $\lambda$H1 is subtracted from the left end peak wavelength $\lambda$Min in order to acquire a wavelength position moving toward an end where the value of the distribution curve corresponding to the peak wavelength decreases by a prescribed ratio (i.e., a half in this case).

FIG. 16 is a flow diagram of processing for setting an acquisition end wavelength of spectral data. The processing as per the flow chart is carried out by the acquisition range setting unit 34 shown by FIG. 14.

In FIG. 16, the acquisition range setting unit 34 first obtains a peak wavelength ($\lambda 3$ in this case) of the fluorescent light in the longest wavelength range (i.e., right side) out of the spectrum characteristic data storage unit 37 to set it for a variable $\lambda$Max; and likewise obtains its half-peak interval (i.e., a displacement from the peak wavelength; $\Delta\lambda 3$ in this case) to set it for a variable $\lambda$H2 (S601).

Then the acquisition range setting unit 34 acquires an acquisition end position, $\lambda$End, for a spectral data based on the following expression (S602):

$$\lambda End = \lambda Max + \lambda H2$$

Here in the step S602, the displacement amount $\lambda$H2 is added to the right end peak wavelength $\lambda$Max in order to acquire a wavelength position being moved toward an end where the value of the distribution curve corresponding to the peak wavelength decreases by a prescribed ratio (i.e., a half in this case).

Note that the processing of FIGS. 15 and 16 for the above described spectrum characteristic data stored by the spectrum characteristic data storage unit 37 will set the following values for the acquisition start position $\lambda$Start and acquisition end position $\lambda$End, respectively:

$$\lambda Start = \lambda Min - \lambda H1 = 510 \text{ nm} - 20 \text{ nm} = 490 \text{ nm}$$

$$\lambda End = \lambda Max + \lambda H2 = 580 \text{ nm} + 10 \text{ nm} = 590 \text{ nm}$$

As described above, the third embodiment makes it possible to set a range of acquiring a valid spectral data automatically for a sample (i.e., specimen) introduced by a plurality of fluorescent probes, thereby lightening a load on the observer who observes the specimen by using a laser scanning microscope.

The following description is about a fourth embodiment in which a setting method for a spectrum resolution is dealt with. The spectrum resolution setting method is the one carried out in the step S204 contained by the flow chart shown by FIG. 7 associated with the first embodiment for example.

In the step S204 shown by FIG. 7, the spectral resolution setting unit 23 sets a slit width (i.e., spectral resolution) $\lambda$Resolution as per the following expression based on a proximate inter-peak wavelength distance $\lambda$GapMin:

$$\lambda Resolution = \lambda GapMin \tag{A1}$$

In the present fourth embodiment, a spectral resolution is calculated (i.e., set) by the following expressions (A2) or (A3), vis-à-vis the above described expression, so that the borders of adjacent sections overlap with each other by a prescribed section.

First, in the expression (A2), a spectral resolution $\lambda$Resolution is calculated by a variable $\lambda$GapMin multiplied by a constant $\beta$ larger than one (i.e., $\beta > 1$):

$$\lambda Resolution = \beta * \lambda GapMin \tag{A2}$$

Next, in the expression (A3), the spectral resolution is calculated by the right side of the above expression (A2) further multiplied by a decreasing function f(I) (where $f(I_1) > f(I_2)$, if $I_1 < I_2$) for a fluorescent intensity I:

$$\lambda Resolution = \beta * f(I) * \lambda GapMin \tag{A3}$$

Here, since f(I) is a decreasing function for a fluorescent intensity I, with its value increasing as a fluorescent intensity of fluorescent probe decreases, resulting in a fluorescent probe having less fluorescent intensity gaining a larger $\lambda$Resolution (i.e., lower spectral resolution), hence gaining more brightness.

The present fourth embodiment has a notable advantage of acquiring a spectral data from a fluorescent probe with a weak fluorescent intensity.

The above described embodiments have a configuration without a limitation about section for one acquisition of spectral data, which is faced with a problem of difficulty in detecting a fluorescent peak if for instance a section of one acquisition becomes very small, however. In order to avoid such situation, the configuration shown by FIGS. 3, 9, 10 or 14 may further comprise a lowest limit resolution value storage unit for storing a lowest limit of spectral resolution which makes a measure for enabling a detection of fluorescent peak and a section width judgment unit for judging whether or not a section width of a section either set or divided into is equal to, or smaller than, the aforementioned lowest limit.

And, if the section width of a section set or divided into is larger than the above described lowest value, the dispersion control unit acquires a spectral data by controlling the dispersion unit based on the section set or divided into.

FIG. 17 is a block diagram with the lowest limit resolution value storage unit 42 and section width judgment unit 41 being added to the block diagram shown by FIG. 3 according to the first embodiment.

Incidentally, the lowest limit resolution value storage unit 42 and section width judgment unit 41 may be added to the block diagram according to the third embodiment shown by FIG. 14 as with the one shown by FIG. 17.

Meanwhile, for the block diagram shown by FIGS. 9 and 10 of the second embodiment, the function of the section width judgment unit 41 may be combined with that of the section judgment unit 31, in which case the section judgment unit 31 compares with the lowest value of section width by referring to the lowest resolution limit value stored by the lowest limit resolution value storage unit 42.

Figure 18:
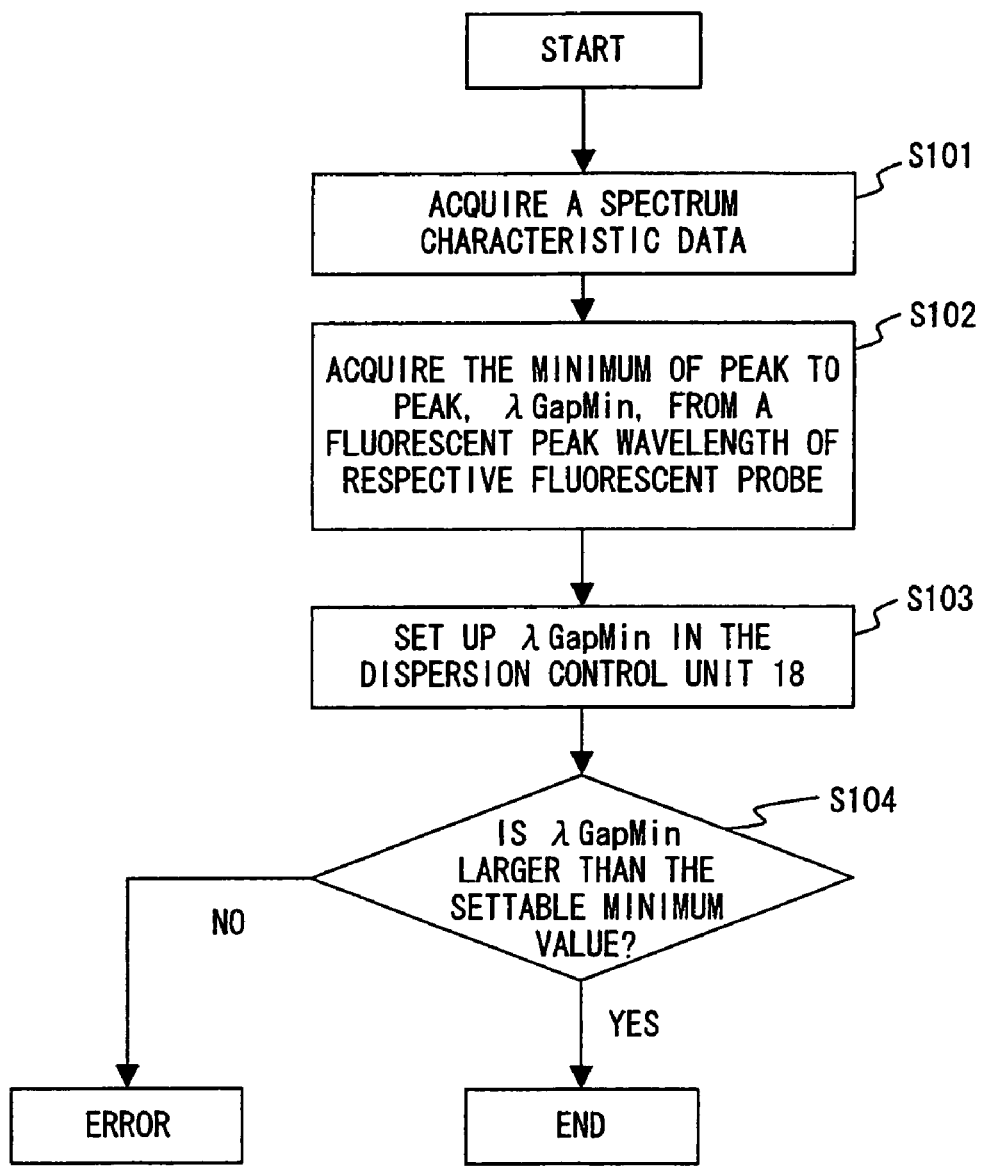
FIG. 18 is a flow chart with a processing for comparing a section width with a lowest limit being added to the one shown by FIG. 6 according to the first embodiment.

FIG. 18 is a flow chart with a processing for comparing a section width with a lowest limit being added to the one shown by FIG. 6 according to the first embodiment.

In FIG. 18, vis-à-vis FIG. 6, added after the step S103 is the step S104 in which the variable λGapMin set in the step S103 is compared with the lowest limit spectral resolution value that indicates the settable minimum value. Then, if the set λGapMin is judged to be larger than the lowest limit spectral resolution value in the judgment step of S104, the processing following that shown by the flow charts of FIG. 7 or 11 will continue and acquire a spectral data based on the set section.

FIG. 19 is a flow chart with a processing for comparing a section width with a lowest limit value being added to the one shown by FIG. 11 according to the second embodiment.

In FIG. 19, vis-à-vis FIG. 11, added between the steps S302 and S203 is the step S303 in which the variable λGapMin re-set in the step S302 is compared with the lowest limit spectral resolution value which indicates the settable minimum value. And, if the re-set λGapMin is judged to be larger than the lowest limit spectral resolution value in the judgment step of S303, the following processes (step S203 etc.) [p1]will continue and acquire a spectral data based on the set section.

Figure 20:
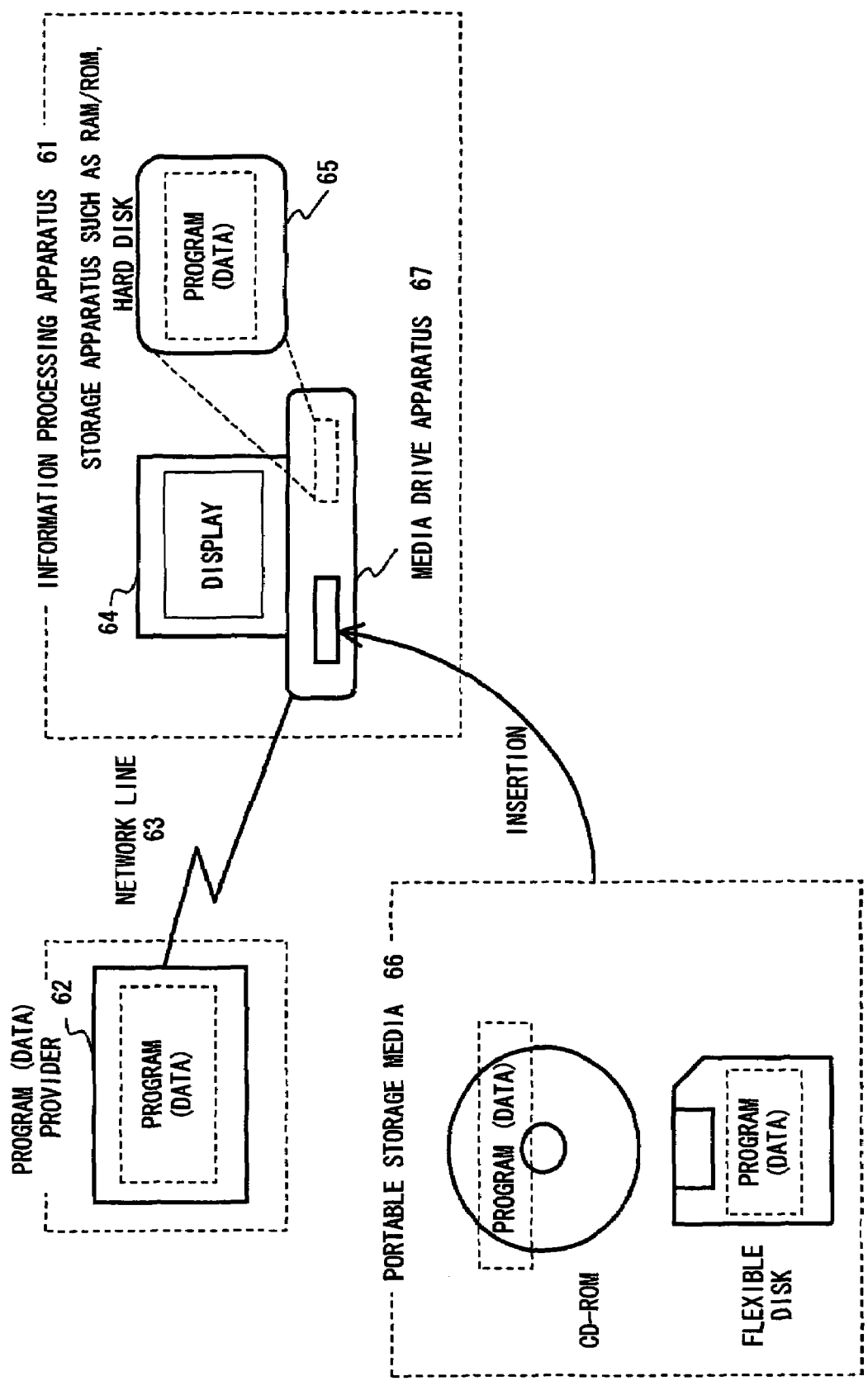
FIG. 20 exemplifies a storage medium.

FIG. 20 exemplifies a storage medium storing a program for making a computer carry out the respective processing according to the present embodiment.

As shown by FIG. 20, the above noted storage medium comprehends a portable storage medium 66, such as CD-ROM, flexible disk (or, may be an MO, DVD, removable hard disk, et cetera) which are detachable with a media drive apparatus 67, a storage unit (e.g., data base) 62 within an external apparatus for transmitting the program by way of a network line 63, and a memory (RAM or hard disk) 65 within a main body 64 of an information processing apparatus 61. The program for carrying out the respective processing according to the present embodiment is executed by loading onto the memory 65 within the main body 64 from the above described storage medium.

What is claimed is:

1. A laser scanning microscope, which enables observation of a specimen, which is marked by a plurality of fluorescent probes, by emitting a laser beam onto the specimen and receiving fluorescent light, corresponding to the emission of the laser beam, back from the specimen, the laser scanning microscope comprising:
    at least one laser source for generating the laser beam in at least one excitation wavelength corresponding to the plurality of fluorescent probes;
    deflector means for scanning the generated laser beam over an observation plane of the specimen;
    dispersion means for dispersing the fluorescent light from the specimen to extract the dispersed fluorescent light by an arbitrary wavelength section;
    spectral data acquisition condition setting means for setting a spectral data acquisition condition for the dispersion means for acquiring spectral data based on spectrum characteristics of the plurality of fluorescent probes;
    dispersion control means for controlling the dispersion means based on the set spectral data acquisition condition; and
    photoelectric conversion means for receiving the extracted fluorescent light and converting the received light into an electrical signal;
    wherein the dispersion means comprises a diffraction mirror for dispersing the fluorescent light from the specimen and selecting a wavelength of the fluorescent light, and a slit which selects the arbitrary wavelength section of the dispersed fluorescent light to be received by the photoelectric conversion means in accordance with the selected wavelength; and
    wherein the spectral data acquisition condition setting means sets a wavelength incrementing amount corresponding to a rotation angle of the diffraction mirror and a spectral resolution corresponding to a width of the slit, which are applicable to carrying out a wavelength scanning for the specimen based on the spectrum characteristics of the plurality of fluorescent probes.

2. A laser scanning microscope, which enables observation of a specimen, which is marked by a plurality of fluorescent probes, by emitting a laser beam onto the specimen and receiving fluorescent light, corresponding to the emission of the laser beam, back from the specimen, the laser scanning microscope comprising:
    at least one laser source which generates the laser beam in at least one excitation wavelength corresponding to the plurality of fluorescent probes;
    a laser beam scanner which scans the generated laser beam over an observation plane of the specimen;
    a dispersion unit which disperses the fluorescent light from the specimen to extract the fluorescent light by an arbitrary wavelength section;
    a spectrum characteristic data storage unit which stores spectrum characteristics of the plurality of fluorescent probes;
    a spectral data acquisition condition setting unit which sets a spectral data acquisition condition for the dispersion unit to extract a prescribed wavelength interval from the fluorescent light based on the spectrum characteristics of the plurality of fluorescent probes;
    a dispersion control unit which controls the dispersion unit based on the set spectral data acquisition condition; and
    a photoelectric conversion unit which receives the extracted fluorescent light, and which converts the received light into an electrical signal;
    wherein the dispersion unit comprises a diffraction mirror for dispersing the fluorescent light from the specimen and selecting a wavelength of the fluorescent light, and a slit for selecting a the arbitrary wavelength section of the dispersed fluorescent light to be received by the photoelectric conversion unit in accordance with the selected wavelength; and
    wherein the spectral data acquisition condition setting unit sets a wavelength incrementing amount corresponding to a rotation angle of the diffraction mirror and a spectral resolution corresponding to a width of the slit, which are applicable to carrying out a wavelength scanning for the specimen based on the spectrum characteristics of the plurality of fluorescent probes.

3. The laser scanning microscope according to claim 2, wherein the spectral data acquisition condition setting unit comprises:
    a proximate inter-peak distance calculation unit for calculating a distance between proximate peak wavelengths among a plurality of peak wavelengths of the fluorescent light from the plurality of fluorescent probes;

an incrementing amount setting unit for setting the wavelength incrementing amount based on the calculated distance between proximate peak wavelengths; and a spectral resolution setting unit for setting the spectral resolution based on the calculated distance between proximate peak wavelengths; and wherein the dispersion control unit controls the dispersion unit based on the set spectral resolution and the set wavelength incrementing amount.

4. The laser scanning microscope according to claim 3, further comprising an acquisition start and end positions specification unit which is adapted to specify acquisition start and end wavelengths of the spectral data.

5. The laser scanning microscope according to claim 3, further comprising an acquisition range setting unit for setting acquisition start and end wavelengths of an acquisition range of the spectral data based on the spectrum characteristics of the plurality of fluorescent probes.

6. The laser scanning microscope according to claim 5, wherein the acquisition range setting unit sets the acquisition range of the spectral data so as to include all of the peak wavelengths of the fluorescent light from the fluorescent probes.

7. The laser scanning microscope according to claim 5, wherein the acquisition range setting unit sets acquisition start or end positions for the spectral data by using a value of wavelength of each edge in curves which decreases by a prescribed ratio from each peak value of curves being the lowest or the highest wavelength.

8. The laser scanning microscope according to claim 3, wherein the wavelength scanning for the specimen obtains the spectral data in a plurality of acquisition sections corresponding to successive wavelength ranges extracted in accordance with the set spectral resolution and incremented by the wavelength incrementing amount, wherein the spectral data acquisition condition setting unit further comprises a section judgment unit for judging whether or not one of the acquisition sections is set so as to include two among: the peak wavelengths of the fluorescent light from the fluorescent probes and any of said at least one excitation wavelength of the laser beam emitted onto the specimen, and wherein the dispersion control unit controls the dispersion unit based on the set acquisition sections if it is judged that each of the acquisition sections includes one or less among: the peak wavelengths of the fluorescent light from the fluorescent probes and any of said at least one excitation wavelength of the laser beam emitted onto the specimen.

9. The laser scanning microscope according to claim 8, wherein the spectral data acquisition condition setting unit further comprises a section division unit for dividing the acquisition sections into a prescribed number if the one of the set acquisition sections is set so as to include at least two among: the peak wavelengths of the fluorescent light from the fluorescent probes and any of said at least one excitation wavelength of the laser beam emitted onto the specimen, wherein the section judgment unit judges whether or not one of the divided acquisition sections includes two among: the peak wavelengths of the fluorescent light from the fluorescent probes and any of said at least one excitation wavelength of the laser beam emitted onto the specimen.

10. The laser scanning microscope according to claim 9, further comprising: a lowest limit resolution value storage unit for storing a lowest limit value of the spectral resolution which enables detection of a peak of fluorescent light; and a section width judgment unit for judging whether or not a section width of into which the acquisition sections are divided by the section division unit is equal to or less than the lowest limit value, wherein the dispersion control unit controls the dispersion unit based on the divided acquisition sections if the section width of is judged to be larger than the lowest limit value.

11. The laser scanning microscope according to claim 3, wherein the wavelength scanning for the specimen obtains the spectral data in a plurality of acquisition sections corresponding to successive wavelength ranges extracted in accordance with the set spectral resolution and incremented by the wavelength incrementing amount, wherein the laser scanning microscope further comprises:
a lowest limit resolution value storage unit for storing a lowest limit value of the spectral resolution which enables detection of a peak of fluorescent light; and a section width judgment unit for judging whether or not a section width the acquisition sections is equal to, or smaller than, the lowest limit value, wherein the dispersion control unit controls the dispersion unit based on the set acquisition sections if the section width is judged to be larger than the lowest limit value.

12. The laser scanning microscope according to claim 3, wherein the wavelength scanning for the specimen obtains the spectral data in a plurality of acquisition sections corresponding to successive wavelength ranges extracted in accordance with the set spectral resolution and incremented by the wavelength incrementing amount, and wherein the spectral resolution setting unit sets the spectral resolution and the wavelength incrementing amount so that borders of the wavelength ranges of adjacent acquisition sections contact with each other.

13. The laser scanning microscope according to claim 3, wherein the wavelength scanning for the specimen obtains the spectral data in a plurality of acquisition sections corresponding to successive wavelength ranges extracted in accordance with the set spectral resolution and incremented by the wavelength incrementing amount, and wherein the spectral resolution setting unit sets the spectral resolution and the wavelength incrementing amount so that the wavelength ranges of adjacent acquisition sections overlap with each other for a prescribed interval.

14. A computer readable storage medium storing a spectral data acquisition program that is executable by a computer to cause the computer to carry out processing for setting a spectral data acquisition condition for acquiring spectral data with a laser scanning microscope which enables observation of a specimen, which is marked by a plurality of fluorescent probes, by emitting a laser beam onto the specimen and receiving fluorescent light, corresponding to the emission of the laser beam, back from the specimen, the program causing the computer carry out a process comprising:

calculating a proximate inter-peak distance between approximate peak wavelengths among a plurality of peak wavelengths of the fluorescent light from the plurality of fluorescent probes;

setting a wavelength incrementing amount corresponding to a rotation angle of a diffraction mirror which disperses the fluorescent light from the specimen into a spectrum and selects a wavelength, based on the calculated proximate inter-peak distance;

setting a spectral resolution corresponding to a slit width of a slit which selects a wavelength section of the received fluorescent light, based on the calculated proximate inter-peak distance; and acquiring the spectral data based on the set wavelength incrementing amount and the set spectral resolution.

15. A method for defining a spectral data acquisition condition and acquiring spectral data with a laser scanning microscope which enables observation of a specimen, which is marked by a plurality of fluorescent probes, by emitting a laser beam onto the specimen and receiving fluorescent light, corresponding to the emission of the laser beam, back from the specimen, the method comprising:

calculating a proximate inter-peak distance between proximate peak wavelengths among a plurality of peak wavelengths of fluorescent light from the plurality of fluorescent probes;

setting a wavelength incrementing amount used for spectrally receiving the fluorescent light back from the specimen based on the calculated proximate inter-peak distance;

setting a spectral resolution which is a wavelength section for one acquisition of the received fluorescent light based on the calculated proximate inter-peak distance; and acquiring the spectral data based on the set wavelength incrementing amount and the set spectral resolution.

16. The spectral data acquisition method according to claim 15, wherein acquiring the spectral data is carried out based on acquisition start and end wavelengths of the spectral data.

17. The spectral data acquisition method according to claim 15, further comprising: setting acquisition start and end wavelengths of the spectral data based on spectrum characteristics of the plurality of fluorescent probes, wherein acquiring the spectral data is carried out based on the acquisition start and end wavelengths of the spectral data.

18. The spectral data acquisition method according to claim 15, wherein the spectral data is obtained in a plurality of acquisition sections, which correspond to wavelength ranges incremented by the wavelength incrementing amount and acquired in successive said acquisitions in accordance with the spectral resolution, and wherein the method further comprises:

judging whether or not one of the acquisition sections is set so as to include two among: the peak wavelengths of the fluorescent light from the fluorescent probes and any of said at least one excitation wavelength of the laser beam emitted onto the specimen, and acquiring the spectral data based on the set acquisition sections sections if it is judged that each of the acquisition sections includes one or less among: the peak wavelengths of the fluorescent light from the fluorescent probes and any of said at least one excitation wavelength of the laser beam emitted onto the specimen.

19. The spectral data acquisition method according to claim 18, further comprising:

dividing the acquisition sections into a prescribed number if the one of the set acquisition sections is set so as to include at least two among: the peak wavelengths of the fluorescent light from the fluorescent probes and any of said at least one excitation wavelength of the laser beam emitted onto the specimen, and judging whether or not one of the divided acquisition sections includes two among: the peak wavelengths of the fluorescent light from the fluorescent probes and any of said at least one excitation wavelength of the laser beam emitted onto the specimen.

20. The spectral data acquisition method according to claim 15, wherein the spectral data is obtained in a plurality of acquisition sections, which correspond to wavelength ranges incremented by the wavelength incrementing amount and acquired in successive said acquisitions in accordance with the spectral resolution, and wherein the method further comprises setting the spectral resolution and the wavelength incrementing amount so that borders of the wavelength ranges of adjacent acquisition sections contact with each other.

21. The spectral data acquisition method according to claim 15, wherein the spectral data is obtained in a plurality of acquisition sections, which correspond to wavelength ranges incremented by the wavelength incrementing amount and acquired in successive said acquisitions in accordance with the spectral resolution, and wherein the method further comprises setting the spectral resolution and the wavelength incrementing amount so that the wavelength ranges of adjacent acquisition sections overlap with each other for a prescribed interval.

22. The spectral data acquisition method according to claim 15, further comprising setting acquisition start or end positions for the spectral data by using a value of wavelength of each edge in curves which decreases by a prescribed ratio from each peak value of curves being the lowest or the highest wavelength.

23. A laser scanning microscope, which enables observation of a specimen, which is marked by a plurality of fluorescent probes, by emitting a laser beam onto the specimen and receiving fluorescent light, corresponding to the emission of the laser beam, back from the specimen, the laser scanning microscope comprising:

proximate inter-peak distance calculation means for calculating a proximate inter-peak distance between proximate peak wavelengths among a plurality of peak wavelengths of fluorescent light from the plurality of fluorescent probes;

incrementing amount setting means for setting a wavelength incrementing amount based on the calculated proximate inter-peak distance;

spectral resolution setting means for setting a spectral resolution which is a wavelength section for receiving fluorescent light based on the calculated proximate inter-peak distance; and spectral data acquisition means for acquiring spectral data based on the set wavelength incrementing amount and the set spectral resolution.

24. A method for defining a spectral data acquisition condition and acquiring spectral data with a laser scanning microscope which enables observation of a specimen, which is marked by a plurality of fluorescent probes, by emitting a laser beam onto the specimen and receiving fluorescent light, corresponding to the emission of the laser beam, back from the specimen, the method comprising:

generating the laser beam in at least one excitation wavelength which corresponds to the plurality of fluorescent probes;

storing spectrum characteristics of the plurality of fluorescent probes;

scanning the generated laser beam over the specimen;
dispersing the fluorescent light from the specimen into a spectrum and selecting a wavelength of the fluorescent light using a diffraction mirror;
extracting the dispersed fluorescent light by an arbitrary wavelength section using a slit, based on the selected wavelength;
setting a wavelength incrementing amount corresponding to a rotation angle of the diffraction mirror and a spectral resolution corresponding to a width of the slit, based on the spectrum characteristics of the plurality of fluorescent probes as a spectral data acquisition condition to acquire the spectral data;
controlling the diffraction mirror and the slit based on the spectral data acquisition condition; and
receiving the extracted fluorescent light and converting the received light into an electric signal.

* * * * *